(12) United States Patent
Cameron et al.

(10) Patent No.: US 11,517,039 B2
(45) Date of Patent: Dec. 6, 2022

(54) WATER-BASED VAPORIZABLE LIQUIDS, METHODS AND SYSTEMS FOR VAPORIZING SAME

(71) Applicant: Lunatech, LLC, Studio City, CA (US)

(72) Inventors: John David Cameron, Studio City, CA (US); Dean Becker, Fairhope, AL (US); Gene Fein, Oxnard, CA (US)

(73) Assignee: Lunatech, LLC, Encino, CA (US)

( * ) Notice: Subject to any disclaimer, the term of this patent is extended or adjusted under 35 U.S.C. 154(b) by 973 days.

(21) Appl. No.: 16/271,599

(22) Filed: Feb. 8, 2019

(65) Prior Publication Data

US 2019/0166903 A1 Jun. 6, 2019

Related U.S. Application Data

(63) Continuation of application No. 15/338,519, filed on Oct. 31, 2016, now abandoned.
(Continued)

(51) Int. Cl.
| | |
|---|---|
| *A61M 16/10* | (2006.01) |
| *A24B 15/167* | (2020.01) |
| *A61K 9/00* | (2006.01) |
| *A61K 9/08* | (2006.01) |
| *A61K 47/10* | (2017.01) |
| *A61K 31/465* | (2006.01) |

(Continued)

(52) U.S. Cl.
CPC ............ *A24B 15/167* (2016.11); *A61B 5/117* (2013.01); *A61K 9/007* (2013.01); *A61K 9/08* (2013.01); *A61K 31/465* (2013.01); *A61K 31/522* (2013.01); *A61K 47/10* (2013.01); *A61M 11/042* (2014.02); *A61M 15/0085* (2013.01); *A61M 15/06* (2013.01); *G06V 30/418* (2022.01); *A24F 40/05* (2020.01); *A24F 40/10* (2020.01); *A24F 40/46* (2020.01); *A24F 40/48* (2020.01); *A24F 40/485* (2020.01); *A61K 47/24* (2013.01); *A61M 2016/0039* (2013.01); *A61M 2205/276* (2013.01); *A61M 2205/3553* (2013.01); *A61M 2205/3592* (2013.01); *A61M 2205/3653* (2013.01); *A61M 2205/505* (2013.01); *A61M 2205/8206* (2013.01)

(58) Field of Classification Search
CPC ........ A24B 15/167; A24F 40/05; A24F 40/10; A24F 40/46; A24F 40/48; A24F 40/485; A61M 2205/276; A61M 2205/505; A61M 2205/3553; A61M 2205/3592; A61M 2205/3653; A61M 2205/8206; A61M 2016/0039; A61M 15/0085; A61M 15/06; A61M 11/042; A61K 47/10; A61K 47/24; A61K 31/522; A61K 31/465; A61K 9/007; A61K 9/08; A61B 5/117; G06V 30/418
USPC ..................................... 128/203.12
See application file for complete search history.

(56) References Cited

U.S. PATENT DOCUMENTS 10,334,888 B2 * 7/2019 Cameron ................ A24F 40/50
10,617,150 B2 * 4/2020 Cameron ............ A61M 11/042
(Continued)

*Primary Examiner* — Khiem M Nguyen
(74) *Attorney, Agent, or Firm* — Kevin Schraven; Anooj Patel; Hankin Patent Law, APC

(57) ABSTRACT

Provided are systems, methods, and liquids related to electronic vapor devices. In one aspect, the application relates to a water-based vaporizable liquid for use in the systems, methods and electronic vapor devices. This abstract is intended as a scanning tool for purposes of searching in the particular art and is not intended to be limiting of the present invention.

20 Claims, 4 Drawing Sheets

Related U.S. Application Data

(60) Provisional application No. 62/249,114, filed on Oct. 30, 2015.

(51) Int. Cl.
*A61M 15/00* (2006.01)
*A61M 15/06* (2006.01)
*A61K 31/522* (2006.01)
*A61M 11/04* (2006.01)
*A61B 5/117* (2016.01)
*G06V 30/418* (2022.01)
*A61K 47/24* (2006.01)
*A61M 16/00* (2006.01)
*A24F 40/05* (2020.01)
*A24F 40/10* (2020.01)
*A24F 40/46* (2020.01)
*A24F 40/48* (2020.01)
*A24F 40/485* (2020.01)

(56) References Cited

U.S. PATENT DOCUMENTS

2019/0090547 A1\* 3/2019 Cameron ............. A24B 15/167
2019/0104762 A1\* 4/2019 Cameron ............... A61K 47/10
2020/0187565 A1\* 6/2020 Williams ............. A61M 11/005

\* cited by examiner

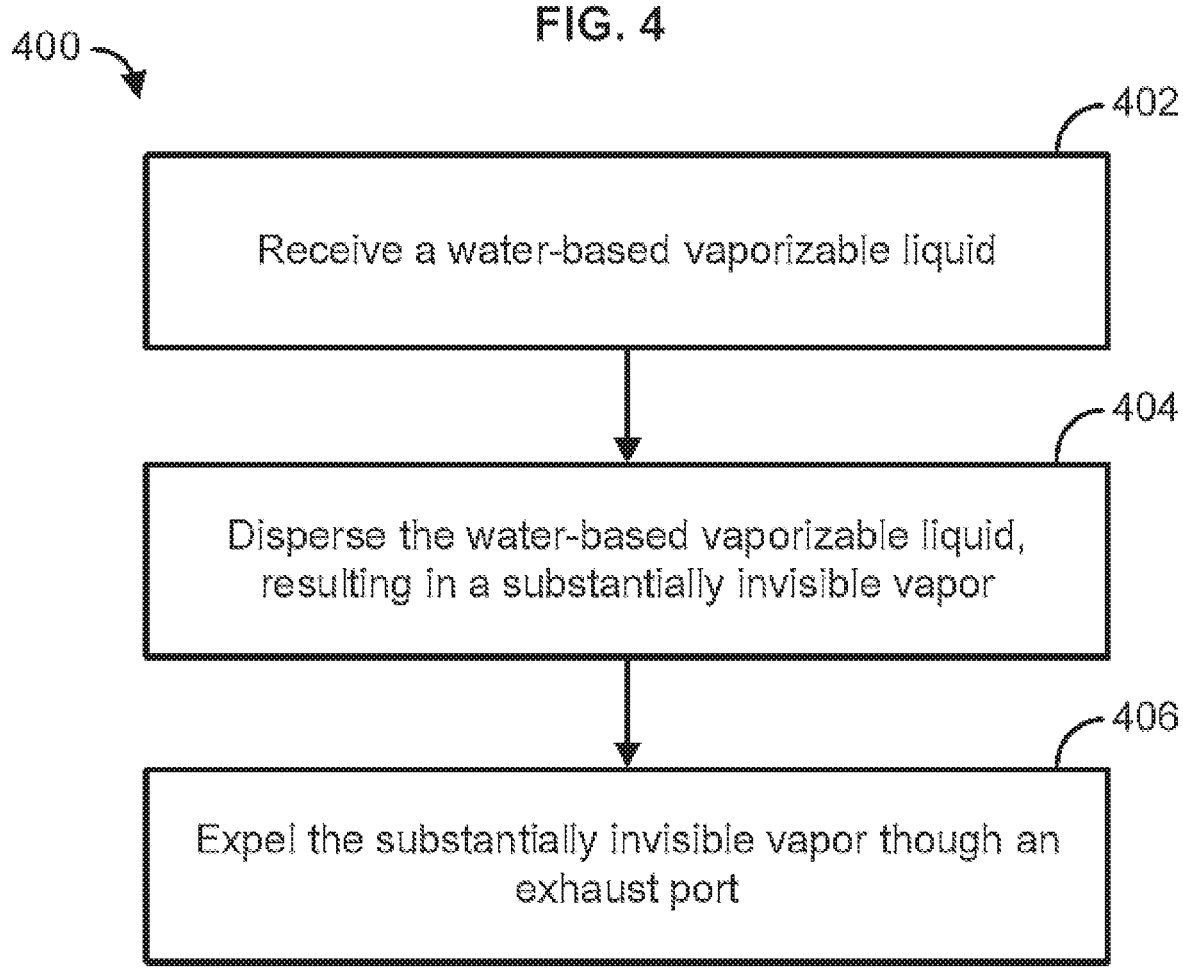

WATER-BASED VAPORIZABLE LIQUIDS, METHODS AND SYSTEMS FOR VAPORIZING SAME

CROSS-REFERENCE TO RELATED APPLICATIONS

This Application claims the benefit of U.S. Non-Provisional patent application Ser. No. 15/338,519, filed on Oct. 31, 2016, which claims the benefit of U.S. Provisional Patent Application No. 62/249,114, filed on Oct. 30, 2015, which are incorporated herein by reference in their entirety.

BACKGROUND

Consumers utilize electronic vapor cigarettes, pipes, and modified vapor devices to enjoy what is commonly known as "vaping." Vaping is an increasingly popular market segment, which has been, and continues to be, steadily gaining market share over the last several years. The fluid utilized for vaping within some electronic vapor devices is commonly known as "eJuice." The eJuice currently utilized in the vaping market contains at least one of propylene glycol (PG) and vegetable glycerin (VG). In fact, a majority of the liquid contained in an eJuice cartridge, chamber, soaked batting system, or other receptacle for eJuice is made up of one or both of PG and/or VG. The PG and/or VG are largely responsible for the vapor plume created by the vaporized eJuice inhaled and exhaled by users. Some users do not enjoy the 'vapor cloud' created by using eJuice containing PG and/or VG in vapor devices. Further, there are consequences associated with the vapor cloud produced by PG and/or VG. Namely, the vapor cloud is an annoyance to many non-vapor users which has triggered subsequent banning of vaping in certain designated areas, such as restaurants, workplaces etc. Additionally, utilizing vapor devices with PG and/or VG creates a large amount of wasted fluid as much of the vapor ends up not absorbed and exhaled into the air.

Despite the widespread population of vaping, eJuice that is substantially free from PG and VG has remained elusive. Thus, there remains a need for vaporizable liquid that produces a substantially invisible vapor cloud and methods of making and using same. These needs and others are met by the present invention.

SUMMARY

In accordance with the purpose(s) of the invention, as embodied and broadly described herein, the invention, in one aspect, relates to vaporizable liquids useful for vaping.

Thus, disclosed are vaporizable liquids which are substantially free of propylene glycol (PG) vegetable glycerin (VG), systems and methods for making and using the disclosed vaporizable liquids. An exemplary vaporizable liquid can comprise at least one solvent and at least one agent selected from a pharmaceutical composition, a nutraceutical composition, and plant extract.

Also disclosed are vaporizable liquid compositions comprising: (a) at least one solvent comprising water, a water-based solution, an alcohol, or a combination thereof; and (b) at least one agent selected from a pharmaceutical composition, a nutraceutical composition, and a plant extract, wherein the vaporizable liquid composition is substantially free of propylene glycol (PG) and vegetable glycerin (VG).

Also disclosed are methods for preparing the disclosed vaporizable liquids can comprise the step of combining a solvent and at least one agent selected from a pharmaceutical composition, a nutraceutical composition, and plant extract, to thereby provide a vaporizable liquid. The vaporizable liquid is substantially free of propylene glycol (PG) vegetable glycerin (VG).

In another aspect, an exemplary system can comprise a dispersion element configured to disperse the disclosed vaporizable liquids to form a vapor or mist such that vapor or mist emitted from the device comprises a substantially invisible vapor trail.

In another aspect, an example method can comprise receiving a disclosed vaporizable liquids at a dispersion element and causing the water-based vaporizable liquid to disperse, resulting in a vapor or mist. The methods further can comprise expelling the vapor or mist through an exhaust port for inhalation by a user. The vapor or mist can be substantially invisible.

Still other objects and advantages of the present disclosure will become readily apparent by those skilled in the art from the following detailed description, wherein it is shown and described only the preferred aspects, simply by way of illustration of the best mode. As will be realized, the disclosure is capable of other and different aspects, and its several details are capable of modifications in various obvious respects, without departing from the disclosure. Accordingly, the description is to be regarded as illustrative in nature and not as restrictive.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

FIG. 4 shows a representative illustration of a method for vaporizing a water-based vaporizable liquid.

Figure 1:
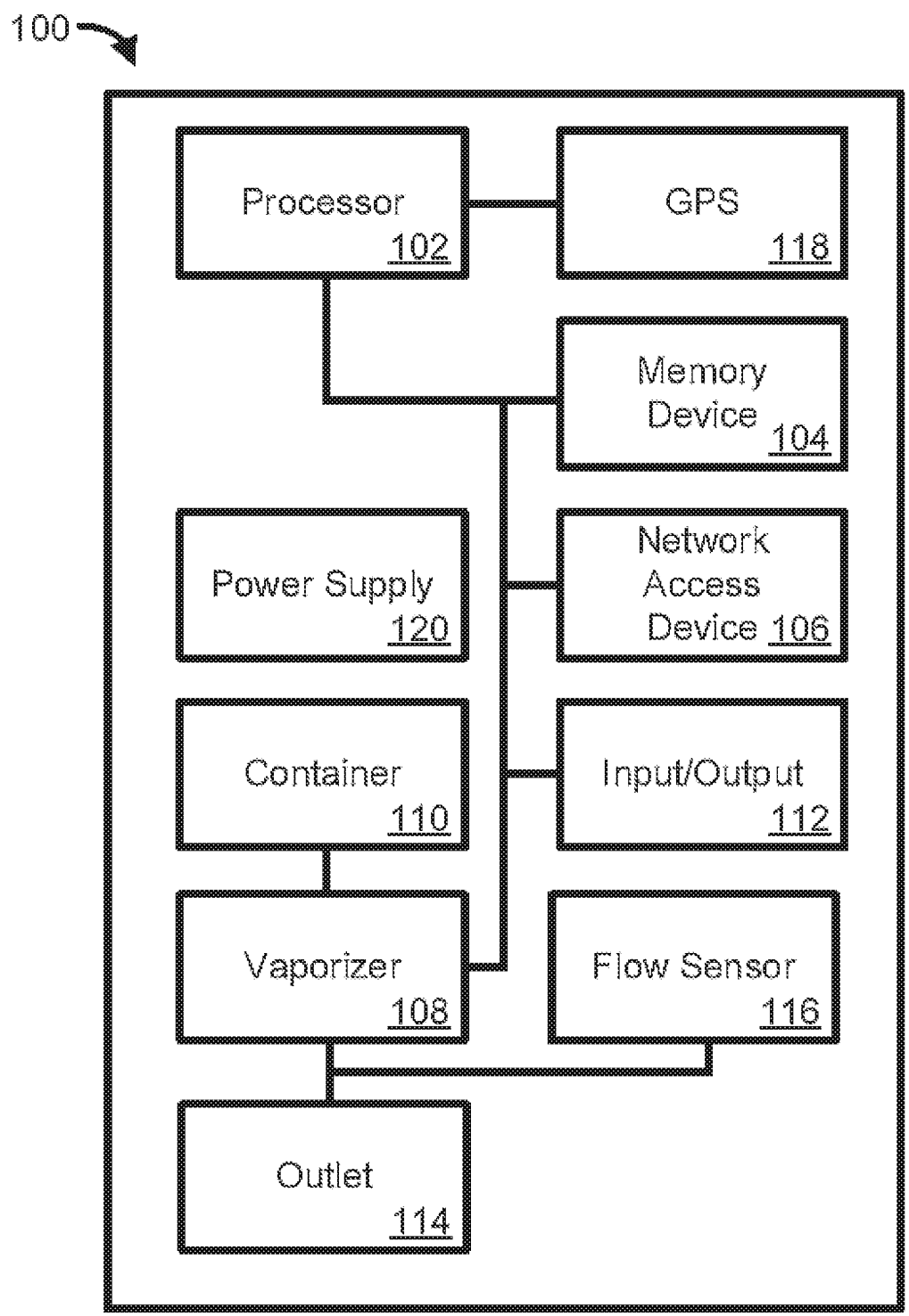
FIG. 1 shows a representative block diagram of an electronic vapor device configured for vaporizing a water-based vaporizable liquid.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present compositions, methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form in order to facilitate describing these aspects.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or wt. %, unless specifically stated to the contrary, is based on the total weight of the formulation or composition in which the component is included.

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

As used herein, the term "substantially," in, for example, the context "substantially free" refers to a composition having less than about 10% by weight, e.g., less than about 5%, less than about 1%, less than about 0.5% by weight, less than about 0.1% by weight, less than about 0.05% by weight, or less than about 0.01% by weight of the stated material, based on the total weight of the composition.

It is further understood that the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components can be present in any ratio predetermined by one of ordinary skill in the art. For example and without limitation, the composition comprising substantially water and natural flavor, unless specifically recited, can comprise water and natural flavor in any ratio predetermined by one of ordinary skill in the art.

As used herein, the terms "electronic liquid," "eLiquid," or "e-liquid" can be used interchangeably and refer to a mixture used in a vapor product, such as an electronic vapor-inhaling device. In some exemplary aspects, an electronic vapor-inhaling device can include without limitation electronic cigarettes, electronic pipes, electronic cigars, and the like.

As used herein, the term "emulsion" is directed to a fine dispersion of minute droplets of one liquid in another in which it is not soluble or miscible.

As used herein, the term "emulsifier" is directed to any substance capable of stabilizing an emulsion. It is understood that in some exemplary aspects, the emulsifier prevents separation of the components present in the emulsion and results in a substantially homogeneous solution.

As used herein, the term "vaporizable," includes and liquids and eJuice that produce 'cold vapor,' such as, for example, mist or dispersion using ultrasonic vibrations, and 'heated vapor,' such as, for example, steam or gas using heating elements.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, "vapor" can include both non-heated vapor (e.g., a mist vapor) and heated vapor. As used herein, "vaporization" can include forming a non-heated vapor (e.g., a mist vapor) as well as forming a heated vapor. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets may be desirable, up to and including 100%. It should further be appreciated that, to simulate smoke, average particle or droplet size may be less than three microns, for example, may be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

As used in this application, the terms "component," "module," "system," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

Disclosed are also components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

B. Vaporizable Liquid Compositions

In one aspect, disclosed are vaporizable liquids comprising at least one solvent comprising water, a water-based solution, an alcohol, or a combination thereof, and at least one agent selected from a pharmaceutical composition, a nutraceutical composition, and plant extract; wherein the vaporizable liquid is substantially free of propylene glycol (PG) vegetable glycerin (VG).

In one aspect, disclosed are vaporizable liquids (eJuice) which are substantially free of propylene glycol (PG) vegetable glycerin (VG). In other aspects, vaporizable liquids are substantially water-based.

In one aspect, disclosed are vaporizable liquid compositions comprising: (a) at least one solvent comprising water, a water-based solution, an alcohol, or a combination thereof; and (b) at least one agent selected from a pharmaceutical composition, a nutraceutical composition, and a plant extract, wherein the vaporizable liquid composition is substantially free of propylene glycol (PG) and vegetable glycerin (VG).

In further aspects, the vaporizable liquid can comprise at least one solvent and at least one agent selected from a pharmaceutical composition, a nutraceutical composition, and plant extract. The vaporizable liquid can be substantially free of propylene glycol (PG) and vegetable glycerin (VG). In still further aspects, the pharmaceutical composition can be pharmacologically active. In yet further aspects, the pharmaceutical composition comprises nicotine, caffeine, a cannabinoid, or a combination thereof.

In a further aspect, the vaporizable liquid composition is substantially free of propylene glycol, vegetable glycerin, or a combination thereof. In a still further aspect, the vaporizable liquid composition is substantially free of propylene glycol. In yet a further aspect, the vaporizable liquid composition is substantially free of vegetable glycerin. In an even further aspect, the vaporizable liquid composition is substantially free of propylene glycol and vegetable glycerin.

In a further aspect, the vaporizable liquid composition comprises less than about 95 wt. % of propylene glycol, less than about 90 wt. % of propylene glycol, less than about 85 wt. % of propylene glycol, less than about 80 wt. % of propylene glycol, less than about 75 wt. % of propylene glycol, less than about 70 wt. % of propylene glycol, less than about 65 wt. % of propylene glycol, less than about 60 wt. % of propylene glycol, less than about 55 wt. % of propylene glycol, less than about 50 wt. % of propylene glycol, less than about 45 wt. % of propylene glycol, less than about 40 wt. % of propylene glycol, less than about 35 wt. % of propylene glycol, less than about 30 wt. % of propylene glycol, less than about 25 wt. % of propylene glycol, less than about 20 wt. % of propylene glycol, less than about 15 wt. % of propylene glycol, less than about 10 wt. % of propylene glycol, and less than about 5 wt. % of propylene glycol.

In a further aspect, the vaporizable liquid composition comprises less than about 95 wt. % of vegetable glycerin, less than about 90 wt. % of vegetable glycerin, less than about 85 wt. % of vegetable glycerin, less than about 80 wt. % of vegetable glycerin, less than about 75 wt. % of vegetable glycerin, less than about 70 wt. % of vegetable glycerin, less than about 65 wt. % of vegetable glycerin, less than about 60 wt. % of vegetable glycerin, less than about 55 wt. % of vegetable glycerin, less than about 50 wt. % of vegetable glycerin, less than about 45 wt. % of vegetable glycerin, less than about 40 wt. % of vegetable glycerin, less than about 35 wt. % of vegetable glycerin, less than about 30 wt. % of vegetable glycerin, less than about 25 wt. % of vegetable glycerin, less than about 20 wt. % of vegetable glycerin, less than about 15 wt. % of vegetable glycerin, less than about 10 wt. % of vegetable glycerin, and less than about 5 wt. % of vegetable glycerin.

In a further aspect, the vaporizable liquid composition comprises less than about 95 wt. % of propylene glycol and vegetable glycerin, less than about 90 wt. % of propylene glycol and vegetable glycerin, less than about 85 wt. % of propylene glycol and vegetable glycerin, less than about 80 wt. % of propylene glycol and vegetable glycerin, less than about 75 wt. % of propylene glycol and vegetable glycerin, less than about 70 wt. % of propylene glycol and vegetable glycerin, less than about 65 wt. % of propylene glycol and vegetable glycerin, less than about 60 wt. % of propylene glycol and vegetable glycerin, less than about 55 wt. % of propylene glycol and vegetable glycerin, less than about 50 wt. % of propylene glycol and vegetable glycerin, less than about 45 wt. % of propylene glycol and vegetable glycerin, less than about 40 wt. % of propylene glycol and vegetable glycerin, less than about 35 wt. % of propylene glycol and vegetable glycerin, less than about 30 wt. % of propylene glycol and vegetable glycerin, less than about 25 wt. % of propylene glycol and vegetable glycerin, less than about 20 wt. % of propylene glycol and vegetable glycerin, less than about 15 wt. % of propylene glycol and vegetable glycerin, less than about 10 wt. % of propylene glycol and vegetable glycerin, and less than about 5 wt. % of propylene glycol and vegetable glycerin.

In a further aspect, the liquid is a colloidal suspension. In a still further aspect, the suspended particles are uniformly dispersed in the solvent.

1. Solvent

In one aspect, the vaporizable liquid composition comprises at least one solvent comprising water, a water-based solution, an alcohol, or a combination thereof. Without wishing to be bound by theory, the solvent composition is selected to increase the solubility of the agent and/or retain the agent in the solution. In this way, the agent can be efficiently vaporized.

The solvent acts as a foundation, dissolving, dispersing, or suspending the additional components of the liquid composition. Upon contacting a heat source, the water or alcohol rapidly vaporizes, leaving behind an aerosol of the remaining ingredients. These ingredients are then carried into the user's lungs, generally because they are bound to or dissolved in the aerosol particles.

In a further aspect, the solvent is water or a water-based solution. In a still further aspect, the solvent is water. In yet a further aspect, the solvent is a water-based solution.

In a further aspect, the solvent is an alcohol. Examples of alcohols include, but are not limited to, methanol, ethanol, propanol, isopropanol, butanol, and tert-butanol.

In a further aspect, the solvent can comprise water, a water-based solution, an alcohol, or another solution that produces sufficient aerosol per volume of liquid. In a still further aspect, the water can be selected from one or more of distilled water, purified water, spring water, tap water, water subjected to reverse osmosis, heated water, water treated with vibrational frequencies including but not limited to sound, cooled water, and water treated with at least one other element.

In further aspects, the solvent can be present in the vaporizable liquid in any desired amount. In still further aspect, the solvent can be present in the liquid in a weight percent of about 10% to about 99.9%, including exemplary subranges of about 10% to about 99%, about 10% to about 98%, about 10% to about 97%, about 10% to about 96%, about 10% to about 95%, about 10% to about 94%, about 10% to about 93%, about 10% to about 92%, about 10% to about 90.1%, about 10% to about 90%, about 10% to about 89%, or about 10% to about 88%. In a yet further aspect, the weight percent can be any value derived from the foregoing values, such as, from about 11.1% to about 99%, about 82.1% to about 93.9%, or about 80.12% to about 98%. In exemplary aspects, the solvent is water and can be present in the liquid in a weight percent of about 84% to about 94%.

In various aspects, the solvent can be combined with at least one of the agent, emulsifier, surfactant, stabilizer, or flavorant, in water soluble or controlled dispersal form. In some aspects, when present, the agent, emulsifier, surfactant, stabilizer, and flavorant are substantially dissolved in the solvent. In other aspects, when present, the agent, emulsifier, surfactant, stabilizer, and flavorant, are suspended in the solvent. In further aspects, the liquid can be a colloidal suspension. In yet further aspects, the suspended particles can be uniformly dispersed in the solvent.

2. Agent

In one aspect, the vaporizable liquid composition comprises at least one agent selected from a pharmaceutical composition, a nutraceutical composition, and a plant extract.

In further aspects, the agent can be present in the vaporizable liquid in any desired amount. In a still further aspect, the agent can be present in the vaporizable liquid in a weight percent of about 0.1% to about 90%, including exemplary subranges of about 0.1% to about 80%, about 0.1% to about 70%, about 0.1% to about 60%, about 0.1% to about 50%, about 0.1% to about 40%, about 0.1% to about 30%, about 0.1% to about 20%, about 0.1% to about 20.1%, about 0.1% to about 20%, about 0.1% to about 19%, about 0.1% to about 18%, about 0.1% to about 17%, about 0.1% to about 16%, about 0.1% to about 15%, about 0.1% to about 14%, about 0.1% to about 13%, about 0.1% to about 12%, about 0.1% to about 10.1%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, or about 0.1% to about 1%. In a yet further aspect, the weight percent can be any value derived from the foregoing values, such as, from about 1.1% to about 10%, about 2.1% to about 9.9%, or about 0.12% to about 88%. In exemplary aspects, the agent can be present in the liquid in a weight percent of about 0.12% to about 0.15%.

In a further aspect, the pharmaceutical composition is pharmacologically active. In a still further aspect, the pharmaceutical composition comprises nicotine, caffeine, a cannabinoid, or a combination thereof.

In a further aspect, the pharmaceutical composition comprises an alkaloid. In a still further aspect, the alkaloid has a pharmacological effect. Examples of alkaloids include, but are not limited to, nicotine, morphine, berberine, vincristine, caffeine, reserpine, galatamine, atropine, vincamine, quinidine, ephedrine, and quinine.

Thus, in various aspects, the pharmaceutical composition comprises an anesthetic. Examples of anesthetics include, but are not limited to, lidocaine, sevoflurane, and propofol.

In various further aspects, the pharmaceutical composition comprises a stimulant. Examples of stimulants include, but are not limited to, caffeine, amphetamine, ephedrine, pseudoephedrine, nicotine, phenylpropanolamine, propylhexedrine, methylphenidate, benzphetamine, and phendimetrazne.

In various further aspects, the pharmaceutical composition comprises an analgesic. Examples of analgesics include, but are not limited to, morphine, methadone, oxymorphone, hydromorphone, levorphanol, oxycodone, meperidine, and fentanyl.

In various further aspects, the pharmaceutical composition comprises an antibacterial agent. Examples of antibacterial agents include, but are not limited to, berberine, penicillin, cephalosporin, polymixin, rifamycin, lipiarmycin, daptomycin, tigecycline, linezolid, and fidaxomicin.

In various further aspects, the pharmaceutical composition comprises an anticancer agent. Examples of anticancer agents include, but are not limited to, vincristine, melphalan, cyclophosphamide, ifosamide, nitrosoureas, alkylsulfonates, ethyleneimines, triazenes, methyl hydrazines, cisplatin, carboplatin, oxaliplatin, methotrexate, 5-fluorouracil, cytarabibe, vinblastine, paclitaxel, docetaxel, etoposide, irinotecan, doxorubicin, bleomycin, L-asparaginase, hydroxyurea, imatinib mesylate, rituximab, epirubicin, bortezomib, zoledronic acid, geftinib, leucovorin, pamidronate, gemcitabine, prednisone, dexamethasone, ethinylestradiol, tamoxifen, megestrol acetate, testosterone propionate, flutamide, bicalutamide, letrozole, anastrazole, finasteride, leuprolide, buserelin, and octreotide.

In various further aspects, the pharmaceutical composition comprises an antihypertension agent. Examples of antihypertension agents include, but are not limited to, reserpine, mecamylamine, guanethidine, moxonidine, methyldopa, guanfacine, guanabenz, clonidine, eplerenone, spironolactone, labetalol, carvedilol, bucindolol, tolazoline, terazosin, prazosin, phenoxybenzamine, indoramin, phentolamine, doxazosin, timolol, propranolol, pindolol, oxprenolol, nebivolol, nadolol, metoprolol, atenolol, fimasartan, valsartan, telmisartan, olmesartan, losartan, irbesartan, eprosartan, candesartan, benazepril, trandolapril, ramipril, quinapril, perindopril, lisinopril, fosinopril, enalapril, captopril, verapamil, diltiazem, nitrendipine, nimodipine, nifedipine, nicardipine, levamlodipine, lercanidipine, isradipine, felodipine, cilnidipine, amlodipine, spironolactone, triamterene, amiloride, metolazone, chlorthalidone, indapamide, bendroflumethiazide, hydrochlorothiazide, chlorothiazide, epitizide, torsemide, furosemide, ethacrynic acid, and bumetanide.

In various further aspects, the pharmaceutical composition comprises a cholinomimeric. Examples of cholinomimerics include, but are not limited to, galantamine, donepezil, edrophonium, neostigmine, physostigmine, pryidostigmine, rivastigmine, tacrine, caffeine, huperzine A, echothiophate, isoflurophate, malathion, cisapride, droperidol, domperidone, metoclopramide, risperidone, paliperidone, trazodone, clonidine, methyldopa, propranolol, atenolol, prazosin, and oxymetazoline.

In various further aspects, the pharmaceutical composition comprises an antispasmodic. Examples of antispasmodics include, but are not limited to, mebeverine and papaverine.

In various further aspects, the pharmaceutical composition comprises a vasodilator. Examples of vasodilators include, but are not limited to, vincamine, nitric oxide, prostacyclin, adenosine, minoxidil, hydralazine, clonidine, terazosin, prazosin, and doxazosin.

In various further aspects, the pharmaceutical composition comprises an anti-arhythmia agent. Examples of anti-arhythmia agents include, but are not limited to, quinidine, amiodarone, flecainide, procainamide, sotalol, metoprolol, and verapamil.

In various aspects, the pharmaceutical composition comprises an anti-asthma agent. Examples of anti-asthma agents include, but are not limited to, ephedrine, beclomethasone dipropionate, budesonide, fluticasone, formoterol, mometasone, prednisone, prednisolone, methylprednisolone, montelukast, zafirlukast, zileuton, mepolizumab, omalizumab, and reslizumab.

In various further aspects, the pharmaceutical composition comprises an antimalarial agent. Examples of antimalarial agents include, but are not limited to, quinine, chloroquine, mefloquine, primaquine, and pyrimethamine.

In various further aspects, the pharmaceutical composition comprises a pharmaceutical agent. Examples of pharmaceutical agents include, but are not limited to, ace inhibitors, such as Benazepril, Captopril, Enalapril, Lisinopril, Moexipril, Perindopril, Quinapril, Ramipril and Trandolapril; acne treatments, such as adapalene, azelaic acid, BenzaClin, Benzamycin, Benzoyl Peroxide, clindamycin, Duac, Erythromycin, Glycolic Acid, Isotretinoin, Sulfacetamide with sulfur, Tazarotene and Tretinoin; actinic keratosis, such as declofenac, fluorouracil; addiction aids, such as buprenorphine, Disulfiram, Naltrexone, Suboxone and varenicline; aldosterone antagonists, such as eplerenone and spironolactone; alpha-1 adrenergic blockers, such as alfuzosin, doxazosin, prazosin, tamsulosin and terazosin; ALS agents, such as riluzole; Alzheimer's Disease medications, such as donepezil, Galantamine, rivastigmine, tacrine and memantine; anesthetics, such as dexmedetomidine, etomidate, ketamine, methohexital, pentobarbital, propofol and thiopental; angiotensin II receptor blockers, such as candesartan, eprosartan mesylate, irbesartan, losartan, olmesartan, telmisartan and valsartan; antacids, such as Aluminum hydroxide, AlOH and magnesium trisilicate; anti-arrhythmics, such as adenosine, amiodarone, Atropine, Bretylium, digoxin-Immune Fab, disopyramide, dofetilide, epinephrine, Esmolol, flecainide, ibutilide, isoproterenol, lidocaine, mexiletine, moricizine, procainamide, propafenone, quinidine, sotalol, tocainide and verapamil; antibiotics, such as Aztreonam, TMP/SMX, Chloramphenicol, Clindamycin, Dapsone, Daptomycin, Ertapenem, Imipenem/cilastatin, Linezolid, Meropenem, Metronidazole, Nitrofurantoin, Quinupristin/Dalfopristin, Rifaximin, Tigecycline, Telithromycin and Tinidazole; anticholinergic acids, such as Dicyclomine, Donnatal, Flavoxate, Glycopyrrolate, Hyoscyamine, Oxybutynin, Propantheline and Tolterodine; anticonvulsants, such as carbamazepine, clonazepam, diazepam, ethosuximide, felbamate, fosphenytoin, gabapentin, levetiracetam, lamotrigine, lorazepam, Oxcarbazepine, Phenobarbital, phenytoin, pregabalin, primidone, tiagabine, topiramate and valproic acid; antidepressants, such as amitriptyline, buprorion, citalopram, desipramine, doxepin, duloxetine, escitalopram, fluoxetine, fluvoxamine, imipramine, mirtazapine, nefazodone, nortriptyline, nortriptyline, sertraline, trazodone and venlafaxine; anti-diarrheals, such as dephenoxylate+atropine, Imodium and bismuth subsalicylate; antiemetics, such as Aprepitant, dolasetron, droperidol, granisetron, metoclopramide, ondansetron, prochlorperazine, scopolamine and trimethobenzamide; antifungals, such as Ampho B, Ampho B lipid, anidulafungin, caspofungin, Clotrimazole fluconazole, flucytosine, Griseofulvin, Itraconazole, ketoconazole, Micafungin, nystatin, Posaconazole, terbinafine, voriconazole, butenafine, ciclopirox, clotrimazole, enconazole, ketoconazole, Miconazole, naftifine, nystatin, oxiconazole terbinafine and Tolnaftate; anti-hepatitis, such as adefovir, entecavir, lamivudine, peginterferon alfa-2a, peginterferon alfa-2b, Rebetron and ribavirin; anti-herpetic agents, such as Acyclovir, famciclovir, valacyclovir, acyclovir, docosanol and penciclovir; antihistamines, such as cetirizine, desloratadine, fexofenadine, loratadine, chlorpheniramine, clemastine, cyproheptadine, dimenhydrinate, diphenhydramine, hydroxzine and promethazine; anti-hypertension, such as Benazepril & HCTZ, Captopril & HCTZ, Enalapril & HCTZ, Lisinopril & HCTZ, Moexipril & HCTZ, Losartan & HCTZ, Valsartan & HCTZ, Atenolol & chlorthalidone, Bisoprolol & HCTZ, Metoprolol & HCTZ, Nadolol & bendroflumethazide, Propranolol & HCTZ, Timolol & HCTZ, Amlodipine & benazepril, Verapamil & trandolapril, Amiloride & HCTZ, Spironolactone & HCTZ, Triamterene & HCTZ, Clonidine & chlorthalidone, Hydralazine & HCTZ, Methyldopa & HCTZ and Prazosin & polythiazide; anti-hypertensives, such as Aliskiren, Aliskiren, epoprostenol, fenoldopam, hydralazine, minoxidil, nitroprusside, phentolamine and treprostinil; anti-influenza agents, such as amantadine, oseltamivir phosphate, rimantadine and zanamivir; anti-malarials/anti-protozoals/amebicides, such as Atovaquone, Chloroquine, Iodoquinol, Mefloquine, Primaquine, Pyrimethamine, Pyrimethamine-Sulfadoxine and Quinine Sulfate; anti-platelet agents, such as abciximab, dipyridamole/ASA, anagrelide, cilostazol, clopidogrel, dipyridamole, eptifabatide, ticlopidine and tirofiban; antipsychotics, such as aripiprazole, chlorpromazine, Clozapine, fluphenazine, haloperidol, loxapine, molindone, olanzepine, perphenazine, pimozide, quetiapine, risperidone, thioridazine, thiothixine, trifluoperazine, ziprasidone and Lithium; antispasmotics, such as Dicyclomine, Donnatal Extentabs, Propantheline, Simethicone, hyoscyamine, Librax, tegaserod and Bellergal-S; anti-tussives/expectorants, such as Benzonatate and guaifenesin; atopic dermatitis medications, such as pimecrolimus and tacrolimus; benzodiazepines and non-benzodiazepine sedatives, such as alprazolam, buspirone, chlordiazepoxide, chlorazepate, clonazepam, diazepam, estazolam, eszcpiclone, flurazepam, lorazepam, midazolam, Oxazepam, ramelteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol and timolol; bile acid sequestrants, such as cholestyramine, colesevelam and colestipol; bisphosphonates, such as alendronate, etidronate, pamidronate, risedronate, tiludronate and Zoledronic acid. Raloxifene and Teriparatide; bladder spasm medications, such as flavoxate, hyoscyamine, darifenacin, oxybutynin, solifenacin, tolterodine and trospium; benign prostatic hypertrophy medications, such as alfuzosin, doxazosin, dutasteride, finasteride, tamsulosin and terazosin; burn preparations, such as mafenide acetate and silver sulfadiazine; calcium channel blockers, such as amlodipine, bepridil, diltiazem, felodipine, isradipine, nicardipine, nifedipine and nisoldipine; calcium supplements, such as Calcium and Hypocalcemia; cephalosporins, such as Cefadroxil, Cefazolin, Cephradine, Cephalexin, Cefaclor, Cefotetan, Cefoxitin, Cefprozil, Cefuroxime, Cefuroxime, Ioracarbef, Cefdinir, Cefixime, Cefoperazone, Cefotaxime, Cefpodoxime, Ceftazidime, Ceftibuten, Ceftizoxime and Cefepime; colony stimulating factors, such as darbepoietin alfa, erythropoietin, filgrastim, oprelvekin, pegfilgrastim and sargramostim; corticosteroids, such as Budesonide, cortisone acetate, dexamethasone, fludrocortisones, hydrocortisone, methylprednisolone and prednisone; corticosteroids Intra-articular, such as Depo-Medrol and Triamcinolone Acetonide; cystitis, such as pentosan polysulfate, Bethanecol and Alum irrigation; decongestants, such as Phenylephrine and Pseudoephedrine; anti-diabetic agents, such as acarbose, Miglitol and metformin, Avandamet®, Glucovance, Metaglip, Metaglip, rosiglitazone, osiglitazone, repaglinide, Chlorpropamide, glimepiride, glyburide, glipizide, Tolazamide, Tolbutamide, Glucagon, extenatide and pramlintide; direct thrombin inhibitors, such as argatroban, Bivalirudin and lepirudin, disease modifying agents, such as adalimumab, anakinra, auranofin, azathioprine, etanercept, hydroxychloroquine, infliximab, leflunomide, methotrexate and sulfasalazine, diuretics, such as Acetazolamide, Amiloride, Amiloride and HCTZ Bendroflumethiazide, Bumetanide, Chlorothiazide, Chlorthalidone, Dichlorphenamide, Eplenerone, Ethacrynic acid, Furosemide, Hydrochlorothiazide, HCTZ/Triampterene, Hydroflumethiazide, Indapamide, Methazolamide, Methyclothiazide, Methyclothiazide, Metolazone, Polythiazide, Spironolactone, Spironolactone, HCTZ Torsemide, Trichlormethiazide and Triamterene; endocrine agents, such as bromoc cinacalcet cosyntropin, riptine, cabergoline, calcitonin, desmopressin, Leuprolide, octreotide and vasopressin; erectile dysfunction agents, such as Sildenafil, tadalafil, vardenafil; fever medications, such as allopurinol, antihistamines, azathioprine, barbiturates, carbamazepine, cephalosporins, cimetidine, folic acid, hydralazine, hydroxyurea, ibuprofen, isoniazid, methyldopa, nitrofurantoin, penicillins, phenytoin, phenytoin, procainamide, prophylthiouracil, quinidine, streptomycin sulfonamides, sulindac, triamterene and vancomycin; fibrates, such as clofibrate, fenofibrat and gemfibrozil; fluoroquinolones, such as Ciprofloxacin, Gatifloxacin, Levofloxacin, Moxifloxacin, Norfloxacin and Ofloxacin; gastrointestinal agents, such as Alosetron, infliximab, Mesalamine, misoprostol, Neomycin, octreotidev, osalazine, Orlistat, sucralafate, Sulfasalazine and vasopressin; gout treatments, such as allopurinol, colchicine, probenecid, Rasburicase and sulfinpyrazone; H2 receptor blockers, such as cimetidine, famotidine, nizatidine and ranitidine; aAnti-herpetic agents, such as Acyclovir, famciclovir, valacyclovir, acyclovir, docosanol and penciclovir; hypertensive urgency, such as Captopril, Clonidine and Labetalol; hypertensive emergency, such as Enalaprilat, Esmolol, Fenoldopam mesylate, Hydralazine, Labetalol, Nicardipine, Nitroglycerin and Sodium nitroprusside; hemorrhoidal preparations, such as Anusol HC, Anusol Suppository, Dibucaine, pramoxine 1%, Proctofoam-HC and Analpram-HC; inflammatory bowel disease agents, such as balsalazide, budesonide, infliximab, mesalamine, olsalazine and sulfasalazine; Interferon, such as Interferon Alfa-2A, Interferon Alfa-2b, Interferon Alfa-2b and Ribavirin combo Pack, Interferon Alfa-N3, Interferon Beta-1A, Interferon Beta-1B (Betaseron); intermittent claudication, such as cilostazol and pentoxifylline; immunizations, such as Comvax, diphtheria-tetanus toxoid, Hepatitis A vaccine, Hepatitis B vaccine, Influenza vaccine, Fluzone, Lyme disease vaccine, PNEUMOVAX* 23; laxatives, such as Bisacodyl, Cascara, Docusate, Fleet Phospho-Soda, Glycerin, Lacalutose, lubiprostone, Magnesium citrate, Magnesium hydroxide-MOM, Mineral Oil, Pericolace, Psyllium and Senna; low molecular weight heparins, such as dalteparin, danaparoid, enoxaparin, tinzaparin, fondaparinux; macrolides, such as Azithromycin, Clarithromycin and Erythromycin; magnesium, such as magnesium salt; migraine treatments, such as almotriptan, eletriptan, frovatriptan, naratriptan, rizatriptan, sumatriptan, zolmitriptan, Cafergot®, Cafergot®, dihydroergotamine and Midrin®; mouth and lip treatments, such as amlexanox, Benzocaine, carbamide, peroxide, Kenalog in Orabase®, Phenol, chlorhexidine gluconate, clotrimazole, Nystatin, Penciclovir, docosanol, Gelclair, lidocaine viscous, BMX Cocktail, Pilocarpine and Artificial saliva; multiple sclerosis treatments, such as glatiramer, interferon beta-1A and interferon beta-1B; muscle relaxants, such as baclofen, carisprodol, cyclobenzaprine, cyclobenzaprine, Diazepam, Metaxalone, Methocarbamol, Orphenadrine; nasal preparations, such as azelastine, beclomethasone, budesonide, cromolyn, desmopressin acetate, flunisolide, fluticasone, Ipratropium bromide, mometasone, oxymetazoline, phenylephrine, Saline nasal spray, Sumatriptan, triamcinolone and Zolmitriptan; urology treatments, such as *Belladonna* and opium, flavoxate, hyoscyamine, hyoscyamine, oxybutynin, solifenacin, tolterodine and trospium; neuromuscular blockers, such as Atracurium, Cisatracurium, doxacurium, mivacurium, pancuronium, Rocuronium, Succinylcholine, vecuronium, Mivacurium, Rapacuronium, Rocuronium, Succinylcholine, Atracurium, Cisatracurium, Pancuronium, Vecuronium, Doxacurium, Pipecuronium and Tubocurarine; nitrates, such as Isosorbide dinitrate, Isosorbide mononitrate, Nitroglycerin ointment, Nitrobid and Nitroglycerin transdermal; NSAIDs, such as Arthrotec, diclofenac, Etodolac, indomethacin, Ketorolac, Sulindac, Tolmentin Diflunisal Salsalate Meloxicam, piroxicam, Nabumetone Flurbiprofen, Ibupropen, Ketoprofen, Naproxen, Oxaprozin, celecoxib, Rofecoxib and Valdecoxib; ophthalmic agents, such as, proparacaine, tetracaine, Ciprofloxacin, Erythromycin, Gentamcyin, levofloxacin, levofloxacin, norfloxacin, Ofloxacin, Polysporin®, Polytrim, Sulfacetamide, Tobramycin, Blephamide®, Blephamide®, Maxitrol®, Pred G® and TobraDex®, Dexamethasone, Fluorometholone, Lotepredenol, Prednisone, Rimexolone, azelastine, Cromolyn sodium, emedastine, Epinastine, Ketotifen Fumarate Ophthalmic Solution 0.025%, Levocabastine, Lodoxamide tromethamine, Naphazoline, Naphcon-A®, nedocromil, Olopatadine, pemirolast, Betaxolol, Betaxolol, Levobunolol, Timolol, Brinzolamide, Dorzolamide, Pilocarpine, bimatoprost, Latanoprost, travoprost, unoprostone, Apraclonidine, Brimonidine, Cosopt® and Cosopt®, Atropine, Cyclopentolate, Homatropine, Phenylephrine, Phenylephrine, Diclofenac, Flurbiprofen and Ketorolac; ear (otic) preparations, such as Auralgan®, carbamide peroxide, CIPRODEX®, Ciprofloxacin and hydrocortisone, Cortisporin®, Ofloxacin, Triethanolamine and Vosol Otic®, opiates, such as Codeine Fentanyl Hydrocodone Hydrocodone, Meperidine Methadone, morhphine, xycodone, Propoxyphene, Darvon®, Fioricet, Fiorinal, Soma compound, Tramadol, Anexsia, Darvocet, Darvon Compound, Lorcet, Lortab, Percocet, Percodan, Roxicet, Tylenol with Codeine. Tylox, Vicodin, Wygesic, Buprenorphene, Butorphanol, Dezocine, Nalbuphine, Pentazocine, Nalmefene Naloxone, Suboxone® and Ziconotide; parkinson's disease treatments, such as amantadine, benztropine, bromocriptine, entacapone, pergolide, pramipexole, ropinirole, selegiline, Sinemet®, tolcapone and trihexyphenidyl; PCA-Patient Controlled Analgesia, such as Fentanyl, Hydromorphone, Meperidine and Morphine; penicillin's, such as Ampicillin, Ampicillin/sulbactam, Amoxicillin, Amoxicillin/Clavulanate, Cloxacillin, Dicloxacillin, Nafcillin, Penicillin G, Penicillin VK, Piperacillin, Piperacillin/Tazobactamm, Ticarcillin, and Ticarcillin/Clavulanate; phosphate supplementation, such as, K-Phos® Neutral Tablets, K-PHOS® ORIGINAL, Neutra-Phos®; potassium supplementation, such as K-LOR, Klor-Con®, Potassium depletion; prostate cancer medications, such as bicalutamide, flutamide, goserelin, leuprolide and nilutamide; proton pump inhibitor's, such as esomeprazole, Lansoprazole, Omeprazole, Pantoprazole and Rabeprazole Sodium; psoriasis medications, such as acitretin, alefacept, Anthralin, Calcipotriene, efalizumab and Tazarotene; renal failure medications, such as Aluminum Hydroxide, Calcium acetate, Calcitriol, Doxercalciferol, Ferric Sodium Gluconate, paricalcitol and sevelamer; pulmonary medications, such as ipratropium, tiotropium, albuterol, bitolterol, levalbuterol, pirbuterol, metaproterenol, formoterol, salmeterol, Advair®, Symbicort®, beclomethasone, budesonide, flunisolide, fluticasone, Mometasone furoate, triamcinolone, montelukast Singulair®, zafirlukast, cromolyn sodium, nedocromil, acetylcysteine and aminophylline/theophylline; disease modifying agents, such as adalimumab, anakinra, auranofin, azathioprine, etanercept, hydroxychloroquine, infliximab, leflunomide, methotrexate and sulfasalazine; HMG COA reductase inhibitors, such as Atorvastatin, Fluvastatin, Lovastatin, Pravastatin, Rosuvastatin, Simvastatin, Advicor®, Vytorin® and ezetimibe; stimulants, such as atomoxetine, benzphetamine, Caffeine, dexmethylphenidate, Dextroamphetamine, diethylpropion, Methylphenidate, Modafinil, Pemoline, phendimetrizine, phentermine and sibutramine; tetracyclines such as Doxycycline, Minocycline and Tetracycline; thrombolytic agents such as Alteplase; anti-thyroid agents such as methimazole and propylthiouracil; toxicology related medications such as acetylcysteine, Charcoal, deferoxamine, digoxin immune fab, flumazenil, fomepizole, methylene blue, naloxone, sodium polystyrene sulfonate and Sorbitol; anti-mycobacterial agents such as Ethambutol, Isoniazid, Pyrazinamide, rifabutin, Rifamate, Rifampin, Rifapentine and Rifater; topical products such as Alitretinoin. Becaplermin, Calamine, Capsaicin, Doxepin, lidocaine/prilocaine, fluorouracil, Masoprocol, Pimecrolimus, Selenium sulfide and Tacrolimus; topical anti-viral agents such as acyclovir, docosanol, imiquimod, penciclovir, podofilox and podophyllin; topical antibacterials such as bacitracin, metronidazole, mupirocin, bacitracin/neomycin/polymyxin, bacitracin/polymyxin and silver sulfadiazine; topical antifungals such as butenafine, ciclopirox, clotrimazole, econazole, ketoconazole, miconazole, naftifine, nystatin, oxiconazole, terbinafine and tolnaftate; topical anti-parasitic agents such as Crotamiton, Lindane, Permethrin, pyrethrins and piperonyl butoxide; topical burn preparations such as mafenide acetate and silver sulfadiazine; topical corticosteroids such as Aclometasone diproprionate, Desonide, Flucinolone acetonide, Hydrocortisone, Betamethasone dipropionate, betamethasone valerate, clocortolone pivalate, desoximetasone, fluocinolone acetonide, flurandrenolide, fluticasone propionate, Chydrocortisone butyrate, hydrocortisone valerate, mometasone furoate, prednicarbate, triamcinolone, amcinonide, augmented betamethasone dipropionate, betamethasone dipropionate, desoximetasone, diflorasone diacetate, fluocinolone acetonide, fluocinonide, halcinonide, clobetasol propionate, diflorasone diacetate and halobetasol propionate; urology medications such as pentosan polysulfate, Bethanecol and phenazopyridine; vaginal preparations such as clindamycin, metronidazole, butoconazole, clotrimazole, miconazole, terconazole and tioconazole; vasodilators such as Fenoldopam mesylate, Hydralazine, Nesiritide, Nicardipine, Nitroglycerin, and Sodium Nitroprusside; and vasopressors and inotropes such as Dobutamine, Dopamine, Epinephrine, inamrinone, Milrinone, Norepinephrine, Phenylephrine, and Vasopressin.

In a further aspect, the nutraceutical composition comprises a vitamin, a mineral, or a combination thereof. In a further aspect, the nutraceutical composition is a vitamin, a mineral, or a combination thereof.

In various further aspects, the nutraceutical composition comprises a nutraceutical agent. Examples of nutraceutical agents include, but are not limited to, constituents in foods or dietary supplements that are responsible for changes in health status, such as components of plants, especially fruits and vegetables, e.g., soy which contains isoflavones and phytoestrogens, tomatoes which contain lycopene that may have anticancer properties, berries such as blueberries and raspberries which contain flavonoids like anthocyanins that may act as antioxidants, green tea which contains epigallocatechin gallate (EGCG) that may have anticancer properties, resveratrol from red grape products as an antioxidant, soluble dietary fiber products, such as *psyllium* seed husk for reducing hypercholesterolemia, broccoli (sulforaphane) as a cancer preventative, and soy or clover (isoflavonoids) to improve arterial health.

In a further aspect, the plant extract includes, but is not limited to a botanical antioxidant, a *cannabis* extract, a tobacco extract, or a combination thereof. In a yet further aspect, the plant extract the plant extract includes, but is not limited to one or more extracts of rosemary, *Echinacea*, currant, propolis, *eucalyptus*, thyme, sage, hornbeam, burdock, sunflower seeds, wood sorrel, red elm, service tree, rhubarb, Japanese mushrooms of the aitake type, turmeric, mangosteen, hyaluronic acid, sodium hyaluronate, mouse-ear hawkweed extract, xanthan gum, plantain and/or plant extracts having mucosal protective effects, *pueraria lobata* (kudzu), or a combination thereof.

In a further aspect, the agent is substantially dissolved in the solvent. In a still further aspect, the agent is suspended in the solvent.

3. Additional Components

In some aspects, the vaporizable liquid can further comprise one or more of an emulsifier, a surfactant, a stabilizer, a flavorant, or a combination thereof. In one aspect, the emulsifier comprises lecithin.

In a further aspect, the vaporizable liquid composition further comprises an emulsifier, a surfactant, a stabilizer, a flavorant, a wellness element, a recreational element, a medicinal element, or a combination thereof. In a still further aspect, the agent, emulsifier, surfactant, stabilizer, and/or flavorant are substantially dissolved in the solvent. In yet a further aspect, the agent, emulsifier, surfactant, stabilizer, and/or flavorant are suspended in the solvent.

In a further aspect, the solvent is combined with at least one of the agent, emulsifier, a surfactant, stabilizer, or flavorant in water soluble or controlled dispersal form.

In further aspects, the vaporizable liquid composition further comprises a stabilizer. In a still further aspect, the stabilizer can comprise a polymer, a sugar, or a combination thereof. In yet a further aspect, the polymer can comprise any desired polymer. Exemplary polymers include, but are not limited to, cellulose, a cellulose derivative, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, ethyl cellulose, hydroxypropyl ethyl cellulose, cellulose acetate phthalate, hydroxypropyl methyl cellulose phthalate, or a combinations thereof. In a yet further aspect, the sugar can comprise any desired sugar. Exemplary sugars include, but are not limited to, glucose, sucrose, maltose, lactose, arabinose, xylose, ribose, fructose, mannose, pentose, galactose sorbose, dextrose, and sugar alcohols, sorbitol, xylitol, mannitol, pentatol, maltitol, isomalt, sucralose, or a combination thereof.

In a further aspect, the vaporizable liquid composition further comprises a flavorant. In a still further aspect, the flavorant can comprise natural flavors, fruit flavors, aromatic flavors, drink flavors, food recipe flavors, candy flavors, floral flavors, or perfumes, spices, and aromas designed to evoke a specific place, or a combination thereof. In yet a further aspect, the flavorant includes, but is not limited to natural flavors, fruit flavors, aromatic flavors, floral flavors, or perfumes, spices, and aromas designed to evoke a specific place, or a combination thereof. In yet a further aspect, exemplary flavorant flavors include, but are not limited to, apple, cherry, green tea, cinnamon, clove, black tea, plum, mango, date, watermelon, coconut, pear, jasmine, peach, fennel, fragrant melon, lychee, mint, chocolate, coffee, cream, banana, almond, grape, strawberry, blueberry, blackberry, pine, kiwi, sapote, taro, lotus, pineapple, orange, lemon, melon, licorice, vanilla, rose, osmanthus, *ginseng*, spearmint, citrus, cucumber, honeydew, walnut, almond, honey, or a combination thereof. In an even further aspect, the flavorant is derived from any natural ingredient that is known to have a pleasant flavor. It is understood that the list of flavorants is not limiting and any flavorants can comprise any component known to provide a pleasant taste to the user.

In various aspects, the flavorant is present in an amount of from about 1 wt. % to about 30 wt. %, including exemplary values of about 3 wt. %, about 5 wt. %, about 10 wt. %, about 15 wt. %, about 20 wt. %, and about 25 wt. %. In yet other aspects, the flavorant can be present in an amount from about 3 wt. % to about 30 wt. %, from about 5 wt. % to about 25 wt. %, or from about 10 wt. % to about 30 wt. %.

In further aspect, the flavorant can be present in the liquid in any desired amount. In still further aspect, the flavorant can be present in the liquid in a weight percent of about 1% to about 80%, including exemplary subranges of about 1% to about 70, about 1% to about 61%, about 1% to about 60%, about 1% to about 50%, about 1% to about 40%, about 1% to about 30%, about 1% to about 20%, about 1% to about 16%, about 1% to about 15%, about 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2%. In a yet further aspect, the weight percent can be any value derived from the foregoing values, such as, from about 1.1% to about 9.9%, about 2.1% to about 23.9%, or about 0.12% to about 30.8%. In exemplary aspects, the flavorant is present in the liquid in a weight percent of about 5% to about 20%. In other aspects, multiple flavorants can be present, such that the vaporizable liquid can have multiple flavors.

In a further aspect, the vaporizable liquid composition further comprises a wellness element. Examples of wellness elements include, but are not limited to, chamomile, *Echinacea*, a homeopathic remedy, an ancient and modern indigenous people's health formula, and a vitamin supplement, or a combination thereof. In a further aspect, the homeopathic remedy can comprise one or more of *Abies Nigra, Carbo vegetablilis, Nux vomica, Robinia pseudoacacia, Arnica Montana, Bryonia, Dulcamara, Pulsatilla, Rhododendron chrysanthum, Rhus tox, Aesculus hippocastanum, Collinsonia Canadensis, Hamamelis virginiana, Phytolacca decandra, Rheum officinale, Dulcamara, Hydrastis Canadensis, Colocynthis, Allium cepa, Apis mellifica, Belladonna Eupatorium perfoliatum, Gelsemium sempervirens, Phytolacca decandra, Pulsatilla. Cimicifuga racemosa, Lycopodium clavatum, Nux moschata, Raphanus sativus, Calendula officinalis, Cineraria maritime, Euphrasia officinalis, Hyoscyamus niger, Nux moschata Passiflora incarnate, Stramonium, Anas barbariae, Arum triphyllum, Belladonna, Phytolacca decandra, Pulsatilla, Spongia tosta, Allium cepa, Ambrosia artemisiaefolia, Sabadilla, Solidago virgaurea, Aconitum napellus, Chelidonium majus, Jequirity, Viburnum opulus, Sanguinaria canadensis, Spigelia anthelmia*, or any combination thereof. In yet a further aspect, the vitamin supplement can include any vitamin supplement known in the art that can be configured for use in an electronic vapor system.

In a further aspect, the wellness element can comprise any ancient and modern indigenous people health formulas. Thus, in various aspects, the wellness element can comprise tobacco, sweetgrass, sage, cedar, laurel, caraway, thyme, or a combination thereof. In a further aspect, the wellness element can comprise various portions of a plant, for example, seeds, berries, roots, leaves, fruits, bark, or flowers. In a still further aspect, the wellness element can comprise the whole plant. Examples of ancient and modern indigenous people health formulas include, but are not limited to, formulas utilized in the traditional Chinese, Korean, Japanese, Native American, Middle Eastern, European, Nepal, Aborigine, African, and Western Pacific medicine.

In a further aspect, the wellness element is present in an amount of from about 0.01 wt. % to about 10 wt. %, including exemplary values of about 0.05 wt. %, about 0.1 wt. %, about 0.3 wt. %, about 0.5 wt. %, about 1 wt. %, about 2 wt. %, about 3 wt. %, about 4 wt. %, about 5 wt. %, about 6 wt. %, about 7 wt. %, about 8 wt. %, and about 9 wt. %. In a still further aspect, the wellness element can be present in any amount that falls between any foregoing values. In yet a further aspect, the wellness element is present in an amount of from about 0.01 wt. % to about 0.3 wt. %, from about 0.1 wt. % to about 5 wt. %, from about 1 wt. % to about 10 wt. %.

In a further aspect, the vaporizable liquid composition further comprises a recreational element. Examples of recreational elements include, but are not limited to, caffeine, nicotine, a *cannabis*-based element, taurine, *salvia*, kratum, and kava, or a combination thereof.

In a further aspect, the recreational element is present in an amount of from about 0.01 wt. % to about 10 wt. %, including exemplary values of about 0.05 wt. %, about 0.1 wt. %, about 0.3 wt. %, about 0.5 wt. %/o, about 1 wt. %, about 2 wt. %, about 3 wt. %, about 4 wt. %, about 5 wt. %, about 6 wt. %, about 7 wt. %, about 8 wt. %, and about 9 wt. %. In a still further aspect, the recreational element can be present in any amount that falls between any foregoing values. In yet a further aspect, the recreational element is present in an amount of from about 0.01 wt. % to about 0.3 wt. %, from about 0.1 wt. % to about 5 wt. %, from about 1 wt. % to about 10 wt. %.

In a further aspect, the vaporizable liquid composition further comprises a medicinal element. Examples of medicinal elements include, but are not limited to, diabetes medications, respiratory medications, sexual dysfunction remedies, and *cannabis*-based medications, or a combination thereof. It is further understood that if combination of medicinal elements are used, the elements present in the final e-liquid solution do not present harmful to health of a user interactions. It is further understood that any medications that can be configured for delivery through the mouth or lungs via the cold vaping system can be utilized.

In a further aspect, the medicinal element is present in an amount of from about 0.01 wt. % to about 10 wt. %, including exemplary values of about 0.05 wt. %, about 0.1 wt. %, about 0.3 wt. %, about 0.5 wt. %, about 1 wt. %, about 2 wt. %, about 3 wt. %, about 4 wt. %, about 5 wt. %, about 6 wt. %, about 7 wt. %, about 8 wt. %, and about 9 wt. %. In a still further aspect, the medicinal element can be present in any amount that falls between any foregoing values. In yet a further aspect, the medicinal element is present in an amount of from about 0.01 wt. % to about 0.3 wt. %, from about 0.1 wt. % to about 5 wt. %, from about 1 wt. % to about 10 wt. %.

In a further aspect, the vaporizable liquid composition further comprises an emulsifier. In a still further aspect, the emulsifier is a natural emulsifier. The emulsifier can be any emulsifier capable of stabilizing an emulsion. Examples of emulsifiers include, but are not limited, to lecithins, natural starches, and sunflower, or a combination thereof. In a still further aspect, the emulsifier is a lecithin. In yet a further aspect, the lecithin is selected from a plant-based lecithin and an animal-based lecithin, or a combination thereof. In an even further aspect, the lecithin is a plant-based lecithin. Examples of plant-based lecithins include, but are not limited to, sunflower lecithins, soybean lecithins, rapeseed lecithins, and cottonseed lecithins, or a combination thereof. In a still further aspect, the lecithin is an animal-based lecithin. Examples of animal-based lecithins include, but are not limited to, egg lecithins, milk lecithins, and marine animal lecithins, or a combination thereof. In yet a further aspect, the lecithin comprises substantially plant-based lecithin. In an even further aspect, the lecithin comprises substantially animal-based lecithin. In a still further aspect, the lecithin comprises both plant-based and animal-based lecithin.

In various aspects, the emulsifier is derived from a sunflower plant. By removing the direct portion of the plant which contains properties of an emulsifier the e-liquid is capable of having an emulsifier which is all natural and in effect, not labeled as an emulsifier but merely labeled as what it is, e.g., a sunflower. This is very significant because chemical emulsifiers such as polysorbate-80 and carboxymethylcellulose, commonly used in packaged foods, drinks, etc. have been found to cause obesity and gut inflammation.

In various aspects, the emulsifier is present in an amount of from about 0.01 wt. % to about 20 wt. %, including exemplary values of about 0.05 wt. %, about 0.1 wt. %, about 0.3 wt. %, about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, and about 19 wt. %. In a further aspect, the emulsifier can be present in any amount that falls between any foregoing values. In a still further aspect, the emulsifier is present in an amount of from about 0.01 wt. % to about 0.3 wt. %, from about 0.1 wt. % to about 15 wt. %, from about 1 wt. % to about 20 wt. %. Without wishing to be bound by theory, the presence of an emulsifier can result in the homogeneous distribution of all of the components present in the vaporizer e-liquid compositions described herein.

In a further aspect, the emulsifier can be present in the liquid in any desired amount. In still further aspect, the emulsifier can be present in the liquid in a weight percent of about 1% to about 80%, including exemplary subranges of about 1% to about 70, about 1% to about 61%, about 1% to about 60%, about 1% to about 50%, about 1% to about 40%, about 1% to about 39%, about 1% to about 38, about 1% to about 30%, about 1% to about 20%, about 1% to about 16%, about 1% to about 15%, about 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2%. In a yet further aspect, the weight percent can be any value derived from the foregoing values, such as, from about 1.1% to about 9.9%, about 2.1% to about 23.9%, or about 0.12% to about 90.8%. In exemplary aspects, the emulsifier is present in the liquid in a weight percent of about 3% to about 10%.

In a further aspect, the surfactant can be present in the liquid in any desired amount. In still further aspect, the surfactant can be present in the liquid in a weight percent of about 1% to about 80%, including exemplary subranges of about 1% to about 70, about 1% to about 61%, about 1% to about 60%, about 1% to about 50%, about 1% to about 40%, about 1% to about 30%, about 1% to about 20%, about 1% to about 16%, about 1% to about 15%, about 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2%. In a yet further aspect, the weight percent can be any value derived from the foregoing values, such as, from about 1.1% to about 9.9%, about 2.1% to about 23.9%, or about 0.12% to about 90.8%. In exemplary aspects, the surfactant is present in the liquid in a weight percent of about 3% to about 10%.

In a further aspect, the vaporizable liquid composition comprises a stabilizer. In a still further aspect, the stabilizer comprises a polymer, a sugar, or a combination thereof. In yet a further aspect, the polymer includes, but is not limited to cellulose, a cellulose derivative, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, ethyl cellulose, hydroxypropyl ethyl cellulose, cellulose acetate phthalate, hydroxypropyl methyl cellulose phthalate, or a combination thereof. In an even further aspect, the sugar includes, but is not limited to glucose, sucrose, maltose, lactose, arabinose, xylose, ribose, fructose, mannose, pentose, galactose sorbose, dextrose, and sugar alcohols, sorbitol, xylitol, mannitol, pentatol, maltitol, isomalt, sucralose, or a combination thereof.

In a further aspect, the stabilizer can be present in the liquid in any desired amount. In still further aspect, the stabilizer can be present in the liquid in a weight percent of about 1% to about 80%, including exemplary subranges of about 1% to about 70, about 1% to about 61%, about 1% to about 60%, about 1% to about 50%, about 1% to about 40%, about 1% to about 30%, about 1% to about 20%, about 1% to about 16%, about 1% to about 15%, about 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2%. In a yet further aspect, the weight percent can be any value derived from the foregoing values, such as, from about 1.1% to about 9.9%, about 2.1% to about 23.9%, or about 0.12% to about 90.8%. In exemplary aspects, the stabilizer is present in the liquid in a weight percent of about 3% to about 10%.

In various aspects, additional elements can be added to the vaporizable liquid composition. In various aspects, these elements can comprise, for example, additives and/or chemicals found in traditional cigarettes. For example, the elements can comprise, but are not limited to, Acetanisole, Acetic Acid, Acetoin, Acetophenone, 6-Acetoxydihydrotheaspirane, 2-Acetyl-3-Ethylpyrazine, 2-Acetyl-5-Methylfuran, Acetylpyrazine, 2-Acetylpyridine, 3-Acetylpyridine, 2-Acetylthiazole, Aconitic Acid, dl-Alanine, Alfalfa Extract, Allspice Extract, Oleoresin, and Oil, Allyl Hexanoate, Allyl Ionone, Almond Bitter Oil, Ambergris Tincture, Ammonia, Ammonium Bicarbonate, Ammonium Hydroxide, Ammonium Phosphate Dibasic, Ammonium Sulfide, Amyl Alcohol, Amyl Butyrate, Amyl Formate, Amyl Octanoate, alpha-Amylcinnamaldehyde, Amyris Oil, trans-Anethole, Angelica Root Extract, Oil and Seed Oil, Anise, Anise Star, Extract and Oils, Anisyl Acetate, Anisyl Alcohol, Anisyl Formate, Anisyl Phenylacetate, Apple Juice Concentrate, Extract, and Skins, Apricot Extract and Juice Concentrate, 1-Arginine, Asafetida Fluid Extract And Oil, Ascorbic Acid, 1-Asparagine Monohydrate, 1-Aspartic Acid, Balsam Peru and Oil, Basil Oil, Bay Leaf, Oil and Sweet Oil, Beeswax White, Beet Juice Concentrate, Benzaldehyde, Benzaldehyde Glyceryl Acetal, Benzoic Acid, Benzoin, Benzoin Resin, Benzophenone, Benzyl Alcohol, Benzyl Benzoate, Benzyl Butyrate, Benzyl Cinnamate, Benzyl Propionate, Benzyl Salicylate, Bergamot Oil, Bisabolene, Black Currant Buds Absolute, Borneol, Bornyl Acetate, Buchu Leaf Oil, 1,3-Butanediol, 2,3-Butanedione, 1-Butanol, 2-Butanone, 4(2-Butenylidene)-3,5,5-Trimethyl-2-Cyclohexen-1-One, Butter, Butter Esters, and Butter Oil, Butyl Acetate, Butyl Butyrate, Butyl Butyryl Lactate, Butyl Isovalerate, Butyl Phenylacetate, Butyl Undecylenate, 3-Butylidenephthalide, Butyric Acid, Cadinene, Caffeine, Calcium Carbonate, Camphene, *Cananga* Oil, *Capsicum* Oleoresin, Caramel Color, Caraway Oil, Carbon Dioxide, Cardamom Oleoresin, Extract, Seed Oil, and Powder, Carob Bean and Extract, beta-Carotene, Carrot Oil, Carvacrol, 4-Carvomenthenol, 1-Carvone, beta-Caryophyllene, beta-Caryophyllene Oxide, Cascarilla Oil and Bark Extract, *Cassia* Bark Oil, Cassie Absolute and Oil, Castoreum Extract, Tincture and Absolute, Cedar Leaf Oil, Cedarwood Oil Terpenes and *Virginiana*, Cedrol, Celery Seed Extract, Solid, Oil, And Oleoresin, Cellulose Fiber, Chamomile Flower Oil And Extract, Chicory Extract, Chocolate, Cinnamaldehyde, Cinnamic Acid, Cinnamon leaf Oil, Bark Oil, and Extract, Cinnamyl Acetate, Cinnamyl Alcohol, Cinnamyl Cinnamate, Cinnamyl Isovalerate, Cinnamyl Propionate, Citral, Citric Acid, Citronella Oil, dl-Citronellol, Citronellyl Butyrate, Citronellyl Isobutyrate, Civet Absolute, Clary Oil, Clover Tops, Red Solid Extract, Cocoa, Cocoa Shells, Extract, Distillate And Powder, Coconut Oil, Coffee, Cognac White and Green Oil, Copaiba Oil, Coriander Extract and Oil, Corn Oil, Corn Silk, Costus Root Oil, Cubeb Oil, Cuminaldehyde, para-Cymene, 1-Cysteine, Dandelion Root Solid Extract, Davana Oil, 2-trans, 4-trans-Decadienal, delta-Decalactone, gamma-Decalactone, Decanal, Decanoic Acid, 1-Decanol, 2-Decenal, Dehydromenthofurolactone, Diethyl Malonate, Diethyl Sebacate, 2,3-Diethylpyrazine, Dihydro Anethole, 5,7-Dihydro-2-Methylthieno(3,4-D) Pyrimidine, Dill Seed Oil and Extract, meta-Dimethoxybenzene, para-Dimethoxybenzene, 2,6-Dimethoxyphenol, Dimethyl Succinate, 3,4-Dimethyl-1,2 Cyclopentanedione, 3,5-Dimethyl-1,2-Cyclopentanedione, 3,7-Dimethyl-1,3,6-Octatriene, 4,5-Dimethyl-3-Hydroxy-2,5-Dihydrofuran-2-One, 6,10-Dimethyl-5,9-Undecadien-2-One, 3,7-Dimethyl-6-Octenoic Acid, 2,4 Dimethylacetophenone, alpha,para-Dimethylbenzyl Alcohol, alpha,alpha-Dimethylphenethyl Acetate, alpha,alpha Dimethylphenethyl Butyrate, 2,3-Dimethylpyrazine, 2,5-Dimethylpyrazine, 2,6 DimethylpyrazinDimethyltetrahydrobenzofuranone, delta-Dodecalactone, gamma-Dodecalactone, Para-Ethoxybenzaldehyde, Ethyl 10-Undecenoate, Ethyl 2-Methylbutyrate, Ethyl Acetate, Ethyl Acetoacetate, Ethyl Alcohol, Ethyl Benzoate, Ethyl Butyrate, Ethyl Cinnamate, Ethyl Decanoate Fenchol, Ethyl Furoate, Ethyl Heptanoate, Ethyl Hexanoate, Ethyl Isovalerate, Ethyl Lactate, Ethyl Laurate, Ethyl Levulinate, Ethyl Maltol, Ethyl Methyl Phenylglycidate, Ethyl Myristate, Ethyl Nonanoate, Ethyl Octadecanoate, Ethyl Octanoate, Ethyl Oleate, Ethyl Palmitate, Ethyl Phenylacetate, Ethyl Propionate, Ethyl Salicylate, Ethyl trans-2-Butenoate, Ethyl Valerate, Ethyl Vanillin, 2-Ethyl (or Methyl)-(3,5 and 6)-Methoxypyrazine, 2-Ethyl-1-Hexanol, 3-Ethyl-2-Hydroxy-2-Cyclopenten-1-One, 2-Ethyl-3, (5 or 6)-Dimethylpyrazine, 5-Ethyl-3-Hydroxy-4-Methyl-2(5H)-Furanone, 2-Ethyl-3-Methylpyrazine, 4-Ethylbenzaldehyde, 4-Ethylguaiacol, para-Ethylphenol, 3-Ethylpyridine, Eucalyptol, Farnesol, D-Fenchone, Fennel Sweet Oil, Fenugreek, Extract, Resin, and Absolute, Fig Juice Concentrate, Food Starch Modified, Furfuryl Mercaptan, 4-(2-Furyl)-3-Buten-2-One, *Galbanum* Oil, Genet Absolute, Gentian Root Extract, Geraniol, Geranium Rose Oil, Geranyl Acetate, Geranyl Butyrate, Geranyl Formate, Geranyl Isovalerate, Geranyl Phenylacetate, Ginger Oil and Oleoresin, 1-Glutamic Acid, 1-Glutamine, Glycerol, Glycyrrhizin Ammoniated, Grape Juice Concentrate, Guaiac Wood Oil, Guaiacol, Guar Gum, 2,4-Heptadienal, gamma-Heptalactone, Heptanoic Acid, 2-Heptanone, 3-Hepten-2-One, 2-Hepten-4-One, 4-Heptenal, trans-2-Heptenal, Heptyl Acetate, omega-6-Hexadecenlactone, gamma-Hexalactone, Hexanal, Hexanoic Acid, 2-Hexen-1-Ol, 3-Hexen-1-Ol, cis-3-Hexen-1-Yl Acetate, 2-Hexenal, 3-Hexenoic Acid, trans-2-Hexenoic Acid, cis-3-Hexenyl Formate, Hexyl 2-Methylbutyrate, Hexyl Acetate, Hexyl Alcohol, Hexyl Phenylacetate, 1-Histidine, Honey, Hops Oil, Hydrolyzed Milk Solids, Hydrolyzed Plant Proteins, 5-Hydroxy-2,4-Decadienoic Acid delta-Lactone, 4-Hydroxy-2,5-Dimethyl-3(2H)-Furanone, 2-Hydroxy-3,5,5-Trimethyl-2-Cyclohexen-1-One, 4-Hydroxy-3-Pentenoic Acid Lactone, 2-Hydroxy-4-Methylbenzaldehyde, 4-Hydroxybutanoic Acid Lactone, Hydroxycitronellal, 6-Hydroxydihydrotheaspirane, 4-(para-Hydroxyphenyl)-2-Butanone, Hyssop Oil, Immortelle Absolute and Extract, alpha-Ionone, beta-Ionone, alpha-Irone, Isoamyl Acetate, Isoamyl Benzoate, Isoamyl Butyrate, Isoamyl Cinnamate, Isoamyl Formate, Isoamyl Hexanoate, Isoamyl Isovalerate. Isoamyl Octanoate, Isoamyl Phenylacetate, Isobornyl Acetate, Isobutyl Acetate, Isobutyl Alcohol, Isobutyl Cinnamate, Isobutyl Phenylacetate, Isobutyl Salicylate, 2-Isobutyl-3-Methoxypyrazine, alpha-Isobutylphenethyl Alcohol, Isobutyraldehyde, Isobutyric Acid, d,l-Isoleucine, alpha-Isomethylionone, 2-Isopropylphenol, Isovaleric Acid, Jasmine Absolute, Concrete and Oil, Kola Nut Extract, Labdanum Absolute and Oleoresin, Lactic Acid, Lauric Acid, Lauric Aldehyde, Lavandin Oil, Lavender Oil, Lemon Oil and Extract, Lemongrass Oil, 1-Leucine, Levulinic Acid, Licorice Root, Fluid, Extract and Powder, Lime Oil, Linalool, Linalool Oxide, Linalyl Acetate, Linden Flowers, Lovage Oil And Extract, 1-Lysine, Mace Powder, Extract and Oil, Magnesium Carbonate, Malic Acid, Malt and Malt Extract, Maltodextrin, Maltol, Maltyl Isobutyrate, Mandarin Oil, Maple Syrup and Concentrate, Mate Leaf, Absolute and Oil, para-Mentha-8-Thiol-3-One, Menthol, Menthone, Menthyl Acetate, dl-Methionine, Methoprene, 2-Methoxy-4-Methylphenol, 2-Methoxy-4-Vinylphenol, para-Methoxybenzaldehyde, 1-(para-Methoxyphenyl)-1-Penten-3-One, 4-(para-Methoxyphenyl)-2-Butanone, 1-(para-Methoxyphenyl)-2-Propanone, Methoxypyrazine, Methyl 2-Furoate, Methyl 2-Octynoate, Methyl 2-Pyrrolyl Ketone, Methyl Anisate, Methyl Anthranilate, Methyl Benzoate, Methyl Cinnamate, Methyl Dihydrojasmonate, Methyl Ester of Rosin, Partially Hydrogenated, Methyl Isovalerate, Methyl Linoleate (48%), Methyl Linolenate (52%) Mixture, Methyl Naphthyl Ketone, Methyl Nicotinate, Methyl Phenylacetate, Methyl Salicylate, Methyl Sulfide, 3-Methyl-1-Cyclopentadecanone, 4-Methyl-1-Phenyl-2-Pentanone, 5-Methyl-2-Phenyl-2-Hexenal, 5-Methyl-2-Thiophenecarboxaldehyde, 6-Methyl-3,-5-Heptadien-2-One, 2-Methyl-3-(para-Isopropylphenyl) Propionaldehyde, 5-Methyl-3-Hexen-2-One, l-Methyl-3Methoxy-4-Isopropylbenzene, 4-Methyl-3-Pentene-2-One, 2-Methyl-4-Phenylbutyraldehyde, 6-Methyl-5-Hepten-2-One, 4-Methyl-5-Thiazoleethanol, 4-Methyl-5-Vinylthiazole, Methyl-trans-2-Butenoic Acid, 4-Methylacetophenone, para-Methylanisole, alpha-Methylbenzyl Acetate, alpha-Methylbenzyl Alcohol, 2-Methylbutyraldehyde, 3-Methylbutyraldehyde, 2-Methylbutyric Acid, alpha-Methylcinnamaldehyde, Methylcyclopentenolone, 2-Methylheptanoic Acid, 2-Methylhexanoic Acid, 3-Methylpentanoic Acid, 4-Methylpentanoic Acid, 2-Methylpyrazine, 5-Methylquinoxaline, 2-Methyltetrahydrofuran-3-One, (Methylthio)Methylpyrazine (Mixture Of Isomers), 3-Methylthiopropionaldehyde, Methyl 3-Methylthiopropionate, 2-Methylvaleric Acid, *Mimosa* Absolute and Extract, Molasses Extract and Tincture, Mountain Maple Solid Extract, Mullein Flowers, Myristaldehyde, Myristic Acid, Myrrh Oil, Beta-Napthyl Ethyl Ether, Nerol, Neroli Bigarde Oil, Nerolidol, Nona-2-trans,6-cis-Dienal, 2,6-Nonadien-1-Ol, gamma-Nonalactone, Nonanal, Nonanoic Acid, Nonanone, trans-2-Nonen-1-Ol, 2-Nonenal, Nonyl Acetate, Nutmeg Powder and Oil, Oak Chips Extract and Oil, Oak Moss Absolute, 9,12-Octadecadienoic Acid (48%) And 9,12, 15-Octadecatrienoic Acid (52%), delta-Octalactone, gamma-Octalactone, Octanal, Octanoic Acid, 1-Octanol, 2-Octanone, 3-Octen-2-One, 1-Octen-3-Ol, 1-Octen-3-Yl Acetate, 2-Octenal, Octyl Isobutyrate, Oleic Acid, Olibanum Oil, Opoponax Oil And Gum, Orange Blossoms Water, Absolute, and Leaf Absolute, Orange Oil and Extract, *Origanum* Oil, Orris Concrete Oil and Root Extract, Palmarosa Oil, Palmitic Acid, Parsley Seed Oil, Patchouli Oil, omega-Pentadecalactone, 2,3-Pentanedione, 2-Pentanone, 4-Pentenoic Acid, 2-Pentylpyridine, Pepper Oil, Black And White, Peppermint Oil, Peruvian (Bois De Rose) Oil, Petitgrain Absolute, Mandarin Oil and Terpeneless Oil, alpha-Phellandrene, 2-Phenenthyl Acetate, Phenenthyl Alcohol, Phenethyl Butyrate, Phenethyl Cinnamate, Phenethyl Isobutyrate, Phenethyl Isovalerate, Phenethyl Phenylacetate, Phenethyl Salicylate, 1-Phenyl-1-Propanol, 3-Phenyl-1-Propanol, 2-Phenyl-2-Butenal, 4-Phenyl-3-Buten-2-Ol, 4-Phenyl-3-Buten-2-One, Phenylacetaldehyde, Phenylacetic Acid, 1-Phenylalanine, 3-Phenylpropionaldehyde, 3-Phenylpropionic Acid, 3-Phenylpropyl Acetate, 3-Phenylpropyl Cinnamate, 2-(3-Phenylpropyl)Tetrahydrofuran, Phosphoric Acid, Pimenta Leaf Oil, Pine Needle Oil, Pine Oil, Scotch, Pineapple Juice Concentrate, alpha-Pinene, beta-Pinene, D-Piperitone, Piperonal, Pipsissewa Leaf Extract, Plum Juice, Potassium Sorbate, 1-Proline, Propenylguaethol, Propionic Acid, Propyl Acetate, Propyl para-Hydroxybenzoate, Propylene Glycol, 3-Propylidenephthalide, Prune Juice and Concentrate, Pyridine, Pyroligneous Acid And Extract, Pyrrole, Pyruvic Acid, Raisin Juice Concentrate, Rhodinol, Rose Absolute and Oil, Rosemary Oil, Rum, Rum Ether, Rye Extract, Sage, Sage Oil, and Sage Oleoresin, Salicylaldehyde, Sandalwood Oil, Yellow, Sclareolide, Skatole, Smoke Flavor, Snakeroot Oil, Sodium Acetate, Sodium Benzoate, Sodium Bicarbonate, Sodium Carbonate, Sodium Chloride, Sodium Citrate, Sodium Hydroxide, Solanone, Spearmint Oil, *Styrax* Extract, Gum and Oil, Sucrose Octaacetate, Sugar Alcohols, Sugars, *Tagetes* Oil, Tannic Acid, Tartaric Acid, Tea Leaf and Absolute, alpha-Terpineol, Terpinolene, Terpinyl Acetate, 5,6,7,8-Tetrahydroquinoxaline, 1,5,5,9-Tetramethyl-13-Oxatricyclo(8.3.0.0(4,9))Tridecane, 2,3,4,5, and 3,4,5,6-Tetramethylethyl-Cyclohexanone, 2,3,5,6-Tetramethylpyrazine, Thiamine Hydrochloride, Thiazole, 1-Threonine, Thyme Oil, White and Red, Thymol, Tobacco Extracts, Tochopherols (mixed), Tolu Balsam Gum and Extract, Tolualdehydes, para-Tolyl 3-Methylbutyrate, para-Tolyl Acetaldehyde, para-Tolyl Acetate, para-Tolyl Isobutyrate, para-Tolyl Phenylacetate, Triacetin, 2-Tridecanone, 2-Tridecenal, Triethyl Citrate, 3,5,5-Trimethyl-1-Hexanol, para,alpha,alpha-Trimethylbenzyl Alcohol, 4-(2,6,6-Trimethylcyclohex-1-Enyl)But-2-En-4-One, 2,6,6-Trimethyl cyclohex-2-Ene-1,4-Dione, 2,6,6-Trimethylcyclohexa-1,3-Dienyl Methan, 4-(2,6,6-Trimethylcyclohexa-1,3-Dienyl) But-2-En-4-One, 2,2,6-Trimethylcyclohexanone, 2,3,5-Trimethylpyrazine, 1-Tyrosine, Delta-Undercalactone, Gamma-Undecalactone, Undecanal, 2-Undecanone, 1, 0-Undecenal, Urea, Valencene, Valeraldehyde, Valerian Root Extract, Oil and Powder, Valeric Acid, gamma-Valerolactone, Valine, Vanilla Extract And Oleoresin, Vanillin, Veratraldehyde, Vetiver Oil, Vinegar, Violet Leaf Absolute, Walnut Hull Extract, Water, Wheat Extract And Flour, Wild Cherry Bark Extract, Wine and Wine Sherry, Xanthan Gum, 3,4-Xylenol, and Yeast. It is further understood that these elements can mimic the feel of real cigarettes to aid in enabling people to stop smoking.

In various aspects, if decreased amount of recreational elements, or elements mimicking the feel of real cigarettes, is required, natural compounds capable of mimicking the sensory experience (e.g., taste, smell, etc.) associated with consumption (e.g., inhalation) of the element can be added. For example, if there is a desire to reduce amount of menthol, the vaporizable liquid composition can comprise an increased concentration of mint, mimicking the sensation of the menthol. In various aspects, a decrease in the concentration of the specific element can require an increase in more than one natural compound.

In a further aspect, emulsifier, surfactant, stabilizer, and/or flavorant are substantially dissolved in the solvent. In a still further aspect, emulsifier, surfactant, stabilizer, and/or flavorant are suspended in the solvent.

In a further aspect, at least one of the additional component(s) are substantially dissolved in the solvent. In a still further aspect, at least one of the additional component(s) are suspended in the solvent.

In a further aspect, the agent, emulsifier, surfactant, stabilizer, and/or flavorant are substantially dissolved in the solvent. In a still further aspect, the agent, emulsifier, surfactant, stabilizer, and/or flavorant are suspended in the solvent.

4. Example Formulations

Without wishing to be bound by theory, Table 1 below shows two examples of water-based eJuice formulations according to the present invention:

TABLE 1

| Component | eJuice Formulation #1 | eJuice Formulation #2 |
|---|---|---|
| Solvent | Water - 90 wt. % | Water - 85 wt. % |
| Agent | Nicotine - 0.12 wt. % | Nicotine - 0.15 wt. % |
| Flavorant | Flavoring - 9.88 wt. % | Flavoring - 9.85 wt. % |
| Emulsifier | — | Lecithin - 5 wt. % |

C. Methods of Making a Vaporizable Liquid

In one aspect, disclosed are methods of preparing vaporizable liquids. In further aspects, the method comprises the step of combining a solvent and at least one agent selected from a pharmaceutical composition, a nutraceutical composition, and a plant extract, thereby providing a vaporizable liquid. The vaporizable liquid is substantially free of propylene glycol (PG) vegetable glycerin (VG). In still further aspects, the solvent is water, a water-based solution, an alcohol, or another solution that produces sufficient aerosol fog per volume of liquid. In some aspects, the method further comprises adding one or more of an emulsifier, a surfactant, a stabilizer, a flavorant, or a combination thereof.

In one aspect, disclosed are methods of making a vaporizable liquid composition, the method comprising the step of combining a solvent and at least one agent selected from a pharmaceutical composition, a nutraceutical composition, and a plant extract, wherein the vaporizable liquid composition is substantially free of propylene glycol (PG) and vegetable glycerin (VG), thereby making a vaporizable liquid composition.

In a further aspect, the solvent is water, a water-based solution, an alcohol, or another solution that produces sufficient aerosol fog per volume of liquid.

In further aspects, the step of combining comprises mixing the liquid using a propeller, a stirrer, or a shaking mechanism. In some aspects, the agent is substantially dissolved in the solvent after the combining step. In other aspects, the agent is suspended in the solvent after the combining step. In still further aspects, the agent remains uniformly dispersed in the solvent after the combining step.

In a further aspect, the vaporizable liquid composition further comprises one or more of a emulsifier, a surfactant, a stabilizer, a flavorant, or a combination thereof. In another aspect, the emulsifier, surfactant, stabilizer, and flavorant are suspended in the solvent after the combining step. In yet another aspect, the emulsifier, surfactant, stabilizer, or flavorant remains uniformly dispersed in the solvent after the combining step.

In a further aspect, the vaporizable liquid composition is substantially free of propylene glycol, vegetable glycerin, or a combination thereof. In a still further aspect, the vaporizable liquid composition is substantially free of propylene glycol. In yet a further aspect, the vaporizable liquid composition is substantially free of vegetable glycerin. In an even further aspect, the vaporizable liquid composition is substantially free of propylene glycol and vegetable glycerin.

In a further aspect, the vaporizable liquid composition comprises less than about 95 wt. % of propylene glycol, less than about 90 wt. % of propylene glycol, less than about 85 wt. % of propylene glycol, less than about 80 wt. % of propylene glycol, less than about 75 wt. % of propylene glycol, less than about 70 wt. % of propylene glycol, less than about 65 wt. % of propylene glycol, less than about 60 wt. % of propylene glycol, less than about 55 wt. % of propylene glycol, less than about 50 wt. % of propylene glycol, less than about 45 wt. % of propylene glycol, less than about 40 wt. % of propylene glycol, less than about 35 wt. % of propylene glycol, less than about 30 wt. % of propylene glycol, less than about 25 wt. % of propylene glycol, less than about 20 wt. % of propylene glycol, less than about 15 wt. % of propylene glycol, less than about 10 wt. % of propylene glycol, and less than about 5 wt. % of propylene glycol.

In a further aspect, the vaporizable liquid composition comprises less than about 95 wt. % of vegetable glycerin, less than about 90 wt. % of vegetable glycerin, less than about 85 wt. % of vegetable glycerin, less than about 80 wt. % of vegetable glycerin, less than about 75 wt. % of vegetable glycerin, less than about 70 wt. % of vegetable glycerin, less than about 65 wt. % of vegetable glycerin, less than about 60 wt. % of vegetable glycerin, less than about 55 wt. % of vegetable glycerin, less than about 50 wt. % of vegetable glycerin, less than about 45 wt. % of vegetable glycerin, less than about 40 wt. % of vegetable glycerin, less than about 35 wt. % of vegetable glycerin, less than about 30 wt. % of vegetable glycerin, less than about 25 wt. % of vegetable glycerin, less than about 20 wt. % of vegetable glycerin, less than about 15 wt. % of vegetable glycerin, less than about 10 wt. % of vegetable glycerin, and less than about 5 wt. % of vegetable glycerin.

In a further aspect, the vaporizable liquid composition comprises less than about 95 wt. % of propylene glycol and vegetable glycerin, less than about 90 wt. % of propylene glycol and vegetable glycerin, less than about 85 wt. % of propylene glycol and vegetable glycerin, less than about 80 wt. % of propylene glycol and vegetable glycerin, less than about 75 wt. % of propylene glycol and vegetable glycerin, less than about 70 wt. % of propylene glycol and vegetable glycerin, less than about 65 wt. % of propylene glycol and vegetable glycerin, less than about 60 wt. % of propylene glycol and vegetable glycerin, less than about 55 wt. % of propylene glycol and vegetable glycerin, less than about 50 wt. % of propylene glycol and vegetable glycerin, less than about 45 wt. % of propylene glycol and vegetable glycerin, less than about 40 wt. % of propylene glycol and vegetable glycerin, less than about 35 wt. % of propylene glycol and vegetable glycerin, less than about 30 wt. % of propylene glycol and vegetable glycerin, less than about 25 wt. % of propylene glycol and vegetable glycerin, less than about 20 wt. % of propylene glycol and vegetable glycerin, less than about 15 wt. % of propylene glycol and vegetable glycerin, less than about 10 wt. % of propylene glycol and vegetable glycerin, and less than about 5 wt. % of propylene glycol and vegetable glycerin.

D. Methods of Volatizing a Vaporizable Liquid

In one aspect, disclosed are methods of volatizing a vaporizable liquid composition, the method comprising the steps of: (a) receiving the vaporizable liquid composition at a dispersing element, wherein the vaporizable liquid composition comprises: (i) at least one solvent comprising water, a water-based solution, an alcohol, or a combination thereof; and (ii) at least one agent selected from a pharmaceutical composition, a nutraceutical composition, and a plant extract, wherein the vaporizable liquid composition is substantially free of propylene glycol (PG) and vegetable glycerin (VG); and (b) dispersing the vaporizable liquid composition, thereby volatizing the composition.

In one aspect, disclosed are methods comprising: receiving a the vaporizable liquid of claim 1 at a dispersing element; dispersing the vaporizable liquid, resulting in a vapor; and expelling the vapor through an exhaust port for inhalation by a user, wherein the vapor is substantially invisible.

In a further aspect, the dispersing element comprises a piezoelectric dispersing element. In a still further aspect, the dispersing element comprises a heated coil element.

In a further aspect, the exhaust port comprises one or more of a plurality of grated exits configured to facilitate the dispersal of vapor, a single opening, and a pump and perforated nozzle system. In a still further aspect, the exhaust port comprises one or more of a plurality of grated exits configured to facilitate the dispersal of vapor, a single opening, and a pump and perforated nozzle system configured to project vapor.

In a further aspect, the method further comprises verifying user information prior to dispersing the vaporizable liquid. In a still further aspect, verifying the user information comprises receiving a transmission comprising the user information and comparing the user information to verification information.

In a further aspect, the vaporizable liquid is received from a container.

In a further aspect, the vaporizable liquid composition is substantially free of propylene glycol, vegetable glycerin, or a combination thereof. In a still further aspect, the vaporizable liquid composition is substantially free of propylene glycol. In yet a further aspect, the vaporizable liquid composition is substantially free of vegetable glycerin. In an even further aspect, the vaporizable liquid composition is substantially free of propylene glycol and vegetable glycerin.

In a further aspect, the vaporizable liquid composition comprises less than about 95 wt. % of propylene glycol, less than about 90 wt. % of propylene glycol, less than about 85 wt. % of propylene glycol, less than about 80 wt. % of propylene glycol, less than about 75 wt. % of propylene glycol, less than about 70 wt. % of propylene glycol, less than about 65 wt. % of propylene glycol, less than about 60 wt. % of propylene glycol, less than about 55 wt. % of propylene glycol, less than about 50 wt. % of propylene glycol, less than about 45 wt. % of propylene glycol, less than about 40 wt. % of propylene glycol, less than about 35 wt. % of propylene glycol, less than about 30 wt. % of propylene glycol, less than about 25 wt. % of propylene glycol, less than about 20 wt. % of propylene glycol, less than about 15 wt. % of propylene glycol, less than about 10 wt. % of propylene glycol, and less than about 5 wt. % of propylene glycol.

In a further aspect, the vaporizable liquid composition comprises less than about 95 wt. % of vegetable glycerin, less than about 90 wt. % of vegetable glycerin, less than about 85 wt. % of vegetable glycerin, less than about 80 wt. % of vegetable glycerin, less than about 75 wt. % of vegetable glycerin, less than about 70 wt. % of vegetable glycerin, less than about 65 wt. % of vegetable glycerin, less than about 60 wt. % of vegetable glycerin, less than about 55 wt. % of vegetable glycerin, less than about 50 wt. % of vegetable glycerin, less than about 45 wt. % of vegetable glycerin, less than about 40 wt. % of vegetable glycerin, less than about 35 wt. % of vegetable glycerin, less than about 30 wt. % of vegetable glycerin, less than about 25 wt. % of vegetable glycerin, less than about 20 wt. % of vegetable glycerin, less than about 15 wt. % of vegetable glycerin, less than about 10 wt. % of vegetable glycerin, and less than about 5 wt. % of vegetable glycerin.

In a further aspect, the vaporizable liquid composition comprises less than about 95 wt. % of propylene glycol and vegetable glycerin, less than about 90 wt. % of propylene glycol and vegetable glycerin, less than about 85 wt. % of propylene glycol and vegetable glycerin, less than about 80 wt. % of propylene glycol and vegetable glycerin, less than about 75 wt. % of propylene glycol and vegetable glycerin, less than about 70 wt. % of propylene glycol and vegetable glycerin, less than about 65 wt. % of propylene glycol and vegetable glycerin, less than about 60 wt. % of propylene glycol and vegetable glycerin, less than about 55 wt. % of propylene glycol and vegetable glycerin, less than about 50 wt. % of propylene glycol and vegetable glycerin, less than about 45 wt. % of propylene glycol and vegetable glycerin, less than about 40 wt. % of propylene glycol and vegetable glycerin, less than about 35 wt. % of propylene glycol and vegetable glycerin, less than about 30 wt. % of propylene glycol and vegetable glycerin, less than about 25 wt. % of propylene glycol and vegetable glycerin, less than about 20 wt. % of propylene glycol and vegetable glycerin, less than about 15 wt. % of propylene glycol and vegetable glycerin, less than about 10 wt. % of propylene glycol and vegetable glycerin, and less than about 5 wt. % of propylene glycol and vegetable glycerin.

E. Electronic Vapor Devices

In one aspect, disclosed are electronic vapor devices for use with a vaporizable fluid.

In one aspect, disclosed are systems, methods, and electronic vapor devices comprising a dispersing element configured to disperse a disclosed vaporizable liquid, such that dispersed liquid emitted from the device produces a substantially invisible vapor trail. In a further aspect, the device is selected from a group consisting of a vape-bot, a robotic vapor device, a micro-vapor device, a vapor pipe, an eCigarette, a hybrid handset and a monocle vapor device.

In a further aspect, the composition is configured for use in an electronic vapor system. Examples of electronic vapor system include, but are not limited to, electronic cigarette, an electronic cigar, an electronic vapor modified device, a hybrid electronic vapor device coupled/integrated with a communication device, an electronic vapor pipe, a micro-sized electronic vapor device, or a robotic electronic vapor device.

In various aspects, the electronic vapor system may be specifically configured for use with a disclosed composition. For example, the system may operate at an output voltage high enough to sufficiently vaporize a disclosed composition. Thus, a system may operate at an output voltage of at least about 2.5V, at least about 3.0V, at least about 3.5V, at least about 4.0V, or at least about 4.5V. In a further aspect, the system may be pressurized. In a still further aspect, the system may be aerosolized.

It is understood that the vaporization e-liquid compositions disclosed herein are not limited to devices operating in e-vapor mode. Thus, in various aspects, the vaporization e-liquid compositions disclosed herein can also be utilized with a hybrid component of an electronic communication handset, for example and without limitation, a cellular telephone or electronic tablet device. In various aspects, the device can comprise a single rechargeable component. In a further aspect, the device is integrated/coupled in continuous electronic communication with any other suitable device. In a still further aspect, the device is a portable device. In yet a further aspect, the device is a disposable device. In an even further aspect, the device is a recyclable device. In a still further aspect, the device is a removable device.

In various aspects, the e-vapor devices can be hard-wired together via an electronic connection at the edges of the devices, wherein there may even be some designed overlap, depending on which way the devices will optimize continuity and function. The metallic electrical connections between devices can be flush or one or both devices can deploy internal connections into the other device via a protruding port penetrating precise fit positioning of the electrical connection leading from one device inside the other device to engage the electrical connection. A locking system may keep the two parts firmly in place, as though the two devices were one.

In some aspects, an eVapor device can utilize the vaporizable fluid (eJuice) disclosed herein. Vaporizing the inventive eJuice by the system can result in a vastly reduced vapor cloud as compared to traditional vaping devices or no visible vapor cloud.

In some aspects, the water-based eJuice can be stored in a fluid container. The fluid container can be a refillable container or a disposable container. The fluid container can comprise anti-microbial and/or anti-bacterial materials within the container (e.g., on an interior surface of the container), such as silver or other anti-microbial and/or anti-bacterial compounds. A top portion of the fluid container can comprise a wick for delivering fluid to a dispersion element system via a pump or other internally initiated pressure-feeding system.

In a further aspect, the device comprises a piezoelectric dispersing element configured to disperse the vaporizable liquid. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the eJuice can be vaporized (e.g., turned into vapor or mist) and the vapor can be dispersed via a system pump and/or a sucking action of the user. In some aspects, the piezoelectric dispersing element can cause dispersion of the eJuice by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the eJuice to disperse, thus forming a vapor or mist from the liquid eJuice. In some aspects, the vapor can be dispersed through a perforated exit to help optimize distribution of the vapor. In some aspects, the eVapor device can further comprise an inhaling mouthpiece. In some aspects, the inhaling mouthpiece can be relatively wide, having a circumference larger than that of conventional inhaling mouthpieces. For example, the mouthpiece can have a circumference of approximately 0.75 inches. This relatively wider mouthpiece can help to enable a wider opening of a user's throat so that more vapor created by the instant invention can reach the lungs.

Because the eJuice is water-based, components of the eJuice are largely water-soluble. Accordingly, once the vapor has reached the lungs, the vapor can be readily absorbed by the alveoli in the lungs much more efficiently than traditional vapor containing PG or VG. In fact, it may take as little as 1/9 (e.g., approximately 11%) of the amount of nicotine in traditional (e.g., PG- and/or VG-based) eJuice to have the same impact for the user.

As disclosed above, the eJuice can further comprise an emulsifier to regulate proper dispersal of ingredients which may not be 100% water soluble. For example, the eJuice can comprise one or more natural emulsifiers such as lecithin. Further, the fluid container can comprise an internal stirring or blending mechanism to help ensure that ingredients are properly dispersed. In other aspects, constituent components, which comprise the eJuice, can be dispersed separately and in tandem, so that the elements can be fed in proper proportions to the wick, which engages the piezoelectric dispersing element.

In some aspects, the eVapor device can have a range of smart features controlled by the processor. The eVapor device can comprise a memory, a storage device, software, and/or a transmitter. These features can allow for monitoring and/or setting adjustments of the instant device, monitoring and control for authorized remote or instant 3rd parties, a full range of social networking functions, ecommerce, integration and information exchange among other eVapor and non-eVapor communication devices and other attendant services. The device can also comprise certain verification features, which allow the user to be verified as to identity and age, helping to prevent under age or otherwise unauthorized users from gaining access to the device. In some aspect, the verification features can be utilized by placing a bottom portion of the eVapor device (the cap) on a smart device (e.g., a smartphone, a handset, a tablet, and the like). The user can verify their identity and registration to the device using the smart device. The software can restrict usage of the device until the verification has occurred. The verification is enabled via a wireless, conductive electrical, or port connection between the eVapor device and the smart device. In some aspects, the smart device can comprise an accessible dossier of user information. In other aspects, the smart device can be verified via an eVapor device system application. Alternatively verification mechanisms can comprise initial verification at a retail location followed by a corresponding, 'voice print', signature, password, security question or fingerprint on the instant device or a networked device.

In a further aspect, the eVapor device can further comprise an on/off switch in electrical communication with the dispersing element; a battery for selectively powering the device; a microprocessor controller electrically coupled to the battery; a storage device coupled to the microprocessor controller; software for execution by the microprocessor controller; a memory configured to store the software, the memory coupled to the microprocessor controller; and a contact point to transmit and verify user data, the contact point coupled to the microprocessor controller. In a still further aspect, the microprocessor controller can comprise one or more of a Kapton based printed microprocessor, a standard eVapor device microprocessor, and a hybrid microprocessor.

In a further aspect, the eVapor device further comprises a wick and pump system powered by a battery and configured to feed the vaporizable liquid into the dispersing element.

In a further aspect, the dispersing element comprises at least one of a piezoelectric dispersing element, a heated coil element, a standard eCigarette dispersing element, and a modified vapor device heating element.

In a further aspect, an exit from the dispersing element comprises at least one of a plurality of grated exits configured to facilitate the dispersal of vapor, a single opening, and a pump and perforated nozzle system configured to project vapor.

In a further aspect, the perforated nozzle system is deployed before or after the dispersing element.

In a further aspect, the vaporizable liquid comprises a container of eLiquid, and wherein the container of eLiquid is at least one of refillable, disposable or replaceable. In a still further aspect, the container comprises internal antibacterial and/or antimicrobial protections, and wherein the antibacterial and/or antimicrobial protections comprise at least one of silver strips, an ultraviolet (UV) light emitting device, and a mixing system configured to enable even dispersal of compounds which comprise the vaporizable liquid.

In a further aspect, the contact point is a bottom end cap of the device configured to contact and communicate with a smart device, and wherein both the device and the smart device comprise software for verifying user data and communicating system data and information.

In a further aspect, the eVapor device further comprises a seal disposed between the mouthpiece and vapor emitted by the dispersing element. In a still further aspect, power is fed from the battery via an infrastructure comprising at least one of a conductive wire, other conductive material, a conductive metal, and other material, and wherein the infrastructure is configured to connect the battery to one or more powered elements of the device. In yet a further aspect, the infrastructure is configured to operate device system functions for one or more of usage meters, gauges, lights, sounds, skin effects, data readings, communications, ecommerce, medical care, and monitoring.

The eVapor device can utilize a stacked design. The bottom portion can comprise a cap, which contains a transmitter to access and verify at least the users' age and identity from a companion smart device. In some aspects, the cap can be cylindrical, having a circumference of approximately 0.75 inches. The cap can be disposed below the processor. In an aspect, the processor can be connected to a system battery disposed immediately above the processor. The processor can also be connected via wiring, coiling or other attendant conductive connections, such as interlocking metal sections, which form the conductive connections to parts of the device requiring power, such as to the piezoelectric dispersing element and system pump, as well as a button which controls at least system on/off settings.

In some aspects, the dispersing element can be fed eJuice as needed by a pressure pump via use of force at a bottom of the eJuice container gradually forcing the bottom of the container to move upwards and forcing the eJuice out of the container as needed. The battery can be any one of standard rechargeable or non-rechargeable batteries currently in use within eVapor devices, as well as batteries which can be charged and/or powered by a crank or kinetic energy, by solar systems, battery exchange or wind systems, or any combination thereof.

The coils can feed a piezoelectric drive circuit to a resident inductor and piezopump. The dispersed (e.g., vaporized) eJuice can be distributed by an additional pump to the eVapor device mouthpiece. Prior to the fluid reaching the mouthpiece, the vapor can flow through a grating to disperse the vapor more effectively. In other aspects, the eJuice can flow through a spray nozzle before or after reaching the dispersing element to form a dispersed vapor. General materials to form a structure of the eVapor device can comprise metals, polymers, natural materials, porcelain, ceramic, smart materials, nano-materials and any combinations thereof. Additional heating and/or cooling systems can be added to the eVapor device to provide heat, cool, or otherwise condition the vapor before it reaches the user.

FIG. 1 is a block diagram of an exemplary electronic vapor device 100 configured for vaporizing the disclosed vaporizable liquid as described herein. The electronic vapor device 100 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vapor device 100 can comprise any suitable housing for enclosing and protecting the various components disclosed herein. The vapor device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 can be printed or otherwise disposed on a circuit board. In some aspects, the circuit board and/or the processor can be formed using a polyimide such as Kapton, or other suitable temperature-resistant material. In other aspects, the processor 102 can comprise a standard eVapor device microprocessor. In still other embodiments, the processor 102 can comprise a hybrid microprocessor comprising elements of a Kapton-based printed microprocessor and a standard microprocessor. The processor 102 can be coupled (e.g., communicatively, operatively, etc. . . . ) to auxiliary devices or modules of the vapor device 100 using a bus or other coupling. The vapor device 100 can comprise a power supply 120. The power supply 120 can comprise one or more batteries and/or other power storage device (e.g., capacitor) and/or a port for connecting to an external power supply. For example, an external power supply can supply power to the vapor device 100 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like. In some aspects, power can be fed from the battery via an infrastructure comprising at least one of a conductive wire, other conductive material, a conductive metal, and other material, and wherein the infrastructure is configured to connect the battery to one or more powered elements of the vapor device 100. In some aspects, the connection between the power supply 120 and one or more of the powered elements (e.g., a vaporizer 108) can be facilitated using one or more conductive coils. The conductive coils can provide an ultrasonic power input to the vaporizer 108. For example, the signal carried by the coil can have a frequency of approximately 107.8 kHz.

The vapor device 100 can comprise a memory device 104 coupled to the processor 102. The memory device 104 can comprise a random access memory (RAM) configured for storing program instructions and data for execution or processing by the processor 102 during control of the vapor device 100. When the vapor device 100 is powered off or in an inactive state, program instructions and data can be stored in a long-term memory, for example, a non-volatile magnetic, optical, or electronic memory storage device (not shown). Either or both of the RAM or the long-term memory can comprise a non-transitory computer-readable medium storing program instructions that, when executed by the processor 102, cause the vapor device 100 to perform all or part of one or more methods and/or operations described herein. Program instructions can be written in any suitable high-level language, for example, C, C++, C# or the Java™, and compiled to produce machine-language code for execution by the processor 102.

In an aspect, the vapor device 100 can comprise a network access device 106 allowing the vapor device 100 to be coupled to one or more ancillary devices (not shown) such as via an access point (not shown) of a wireless telephone network, local area network, or other coupling to a wide area network, for example, the Internet. In that regard, the processor 102 can be configured to share data with the one or more ancillary devices via the network access device 106. The shared data can comprise, for example, usage data and/or operational data of the vapor device 100, a status of the vapor device 100, a status and/or operating condition of one or more the components of the vapor device 100, text to be used in a message, a product order, payment information, and/or any other data. Similarly, the processor 102 can be configured to receive control instructions from the one or more ancillary devices via the network access device 106. For example, a configuration of the vapor device 100, an operation of the vapor device 100, and/or other settings of the vapor device 100, can be controlled by the one or more ancillary devices via the network access device 106. For example, an ancillary device can comprise a server that can provide various services and another ancillary device can comprise a smartphone for controlling operation of the vapor device 100. In some aspects, the smartphone or another ancillary device can be used as a primary input/output of the vapor device 100 such that data is received by the vapor device 100 from the server, transmitted to the smartphone, and output on a display of the smartphone.

In an aspect, the vapor device 100 can comprise a vaporizer 108. The vaporizer 108 can be coupled to one or more containers 110. Each of the one or more containers 110 can be configured to hold one or more vaporizable or non-vaporizable materials. The vaporizer 108 can receive the one or more vaporizable or non-vaporizable materials from the one or more containers 110 and cause vaporization (e.g., dispersion) of the one or more vaporizable or non-vaporizable materials until the one or more vaporizable or non-vaporizable materials achieve a vapor state. In various aspects, the vaporizer 108 can comprise one or more of a piezoelectric dispersing element, a heated coil element, a standard eCigarette dispersing element, a modified vapor device heating element, and the like. In some aspects, the piezoelectric dispersing element can receive the ultrasonic signal transmitted from the power supply 120 through the coils, and can induce vibration (and thus dispersion and vaporization) of the eJuice. An ultrasonic electric field applied to a piezoelectric material within the piezoelectric element causes ultrasonic expansion and contraction of the piezoelectric material, resulting in ultrasonic vibrations according to the frequency of the signal. The vaporizable and non-vaporizable materials can be dispersed (e.g., vaporized, turned to mist, etc.) by the piezoelectric dispersing element, thus forming a vapor or mist. In various embodiments, instead of heating the one or more vaporizable or non-vaporizable materials, the vaporizer 108 can nebulize or otherwise cause the one or more vaporizable or non-vaporizable materials in the one or more containers 110 to reduce in size into particulates. In various embodiments, the one or more containers 110 can comprise a compressed liquid that can be released to the vaporizer 108 via a valve or another mechanism. In various embodiments, the one or more containers 110 can comprise a wick (not shown) through which the one or more vaporizable or non-vaporizable materials are drawn to the vaporizer 108. The one or more containers 110 can be made of any suitable structural material, such as, an organic polymer, metal, ceramic, composite, or glass material. In some aspects, the one or more containers 110 can comprise one or more refillable containers, one or more disposable containers, and or one or more replaceable containers. In various aspects, the one or more containers 110 can comprise internal structures that provide antibacterial or antimicrobial protections. For example, the structures can comprise at least one of silver strips and an ultraviolet (UV) light emitting device. The one or more containers 110 can further comprise a mixing system to enable even dispersal of components of the liquid.

In some aspects, the liquid can comprise a liquid which, when vaporized produces a drastically reduced vapor cloud when compared to traditional eJuice or a liquid which, when vaporized, produces a substantially invisible vapor. For example, the liquid can comprise a water-based eJuice. In an aspect, the water-based eJuice can be an eJuice having water as the primary compound therein. In some aspects, the water can be combined with one or more of a flavoring, nicotine, medication, wellness elements, aromatherapy elements (e.g., perfumes, flowers, spices, mint or aromas of a specific place and/or time, such as by way of example Fenway Park in Boston or Paris in the spring) and legal recreational elements in water soluble or controlled dispersal form. In some aspects, the water-based eJuice can be substantially free of propylene glycol (PG) and/or vegetable glycerin (VG). The water can be distilled water, purified water, spring water, tap water, water subjected to reverse osmosis, heated water, water treated with vibrational frequencies including but not limited to sound, cooled water, or water treated with at least one other element.

In an aspect, the vapor device 100 can also comprise an input/output device 112 coupled to one or more of the processor 102, the vaporizer 108, the network access device 106, and/or any other electronic component of the vapor device 100. Input can be received from a user or another device and/or output can be provided to a user or another device via the input/output device 112. The input/output device 112 can comprise any combinations of input and/or output devices such as buttons, knobs, keyboards, touch-screens, displays, light-emitting elements, a speaker, and/or the like. In an aspect, the input/output device 112 can comprise an interface port (not shown) such as a wired interface, for example a serial port, a Universal Serial Bus (USB) port, an Ethernet port, or other suitable wired connection. The input/output device 112 can comprise a wireless interface (not shown), for example a transceiver using any suitable wireless protocol, for example WiFi (IEEE 802.11), Bluetooth®, infrared, or other wireless standard. For example, the input/output device 112 can communicate with a smartphone via Bluetooth® such that the inputs and outputs of the smartphone can be used by the user to interface with the vapor device 100.

Input from the input/output device 112 can be used by the processor 102 to cause the vaporizer 108 to disperse the one or more vaporizable or non-vaporizable materials. For example, a user can depress a button, causing the vaporizer 108 to start dispersing the one or more vaporizable or non-vaporizable materials. In some aspects, the input/output device 112 can also be used to receive user information (e.g., from a user smart device). The user information can be verified by the processor 102. The eVapor device 100 and/or the smart device can comprise software for verifying the user data. The input/output device 112 can also be used to operate device system functions for one or more of usage meters, gauges, lights, sounds, skin effects, data readings, communications, ecommerce, medical care, and monitoring.

A user can then draw on an outlet 114 to inhale the vapor. In some aspects, vapor exiting the vaporizer 108 toward the outlet 114 can flow through one or more grated exits to facilitate dispersal of the vapor. In other aspects the vapor can flow through a single opening. In still other aspects, the eJuice can be projected via a pump and a perforated nozzle before or after passing through the vaporizer 108. In various aspects, the processor 102 can control vapor production and flow to the outlet 114 based on data detected by a flow sensor 116. For example, as a user draws on the outlet 114, the flow sensor 116 can detect the resultant pressure and provide a signal to the processor 102. In response, the processor 102 can cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. In some aspects the outlet 114 can comprise a mouthpiece. The mouthpiece can have a circumference greater than that of a traditional eVapor device mouthpiece. For example, the mouthpiece can have a circumference of approximately 0.75 inches. In some aspects, a seal (not shown) can be disposed between the vaporizer 108 and the outlet 114.

In an aspect, the vapor device 100 can comprise a global positioning system (GPS) unit 118. The GPS 109 can detect a current location of the device 100. In some aspects, a user can request access to one or more services that rely on a current location of the user. For example, the processor 102 can receive location data from the GPS 109, convert it to usable data, and transmit the usable data to the one or more services via the network access device 106. GPS unit 118 can receive position information from a constellation of satellites operated by the U.S. Department of Defense. Alternately, the GPS unit 118 can be a GLONASS receiver operated by the Russian Federation Ministry of Defense, or any other positioning device capable of providing accurate location information (for example, LORAN, inertial navigation, and the like). The GPS unit 118 can contain additional logic, either software, hardware or both to receive the Wide Area Augmentation System (WAAS) signals, operated by the Federal Aviation Administration, to correct dithering errors and provide the most accurate location possible. Overall accuracy of the positioning equipment subsystem containing WAAS is generally in the two meter range.

Figure 2:
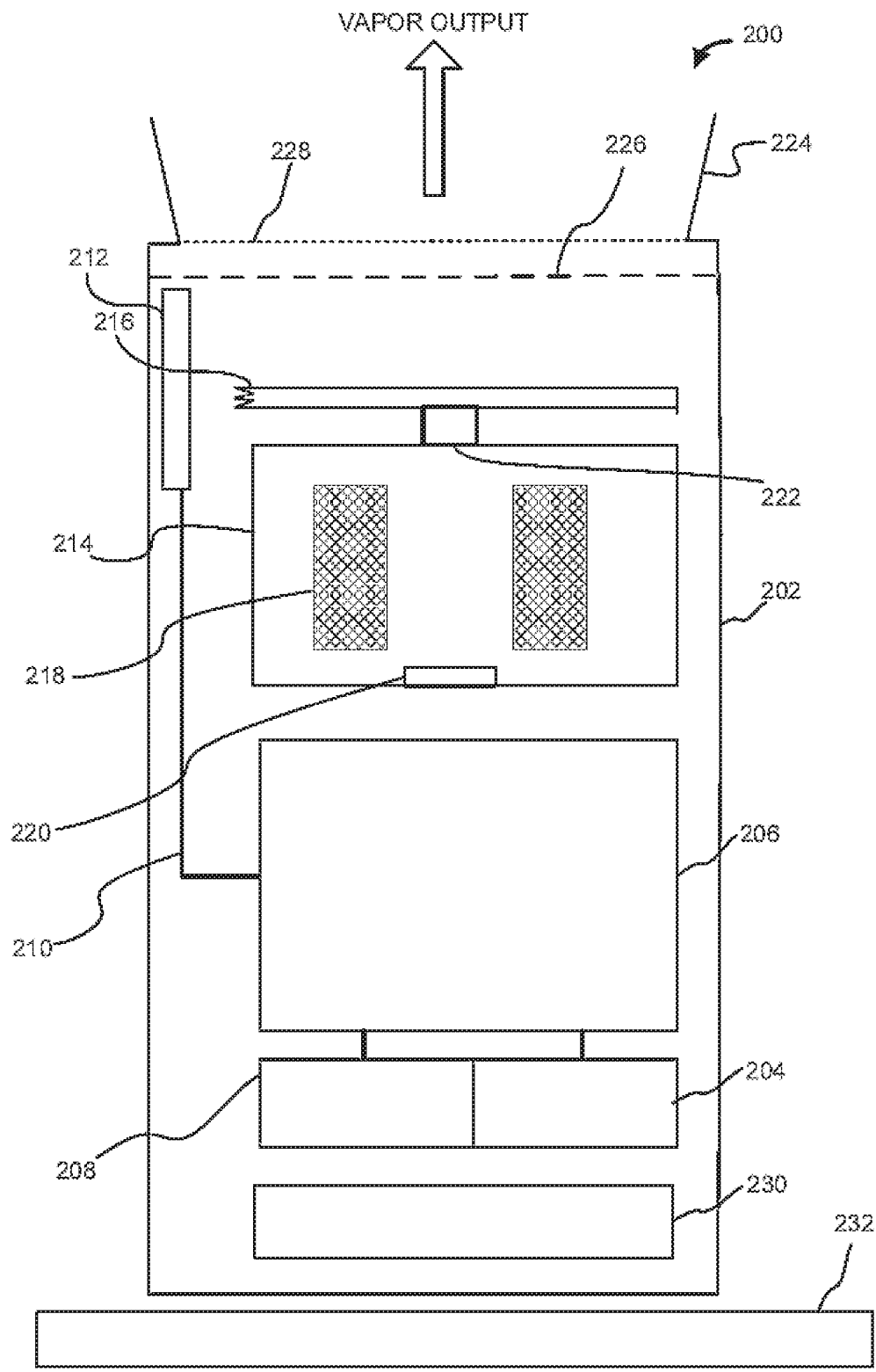
FIG. 2 shows a representative illustration of a vapor device configured for vaporizing a water-based vaporizable liquid.
Figure 3:
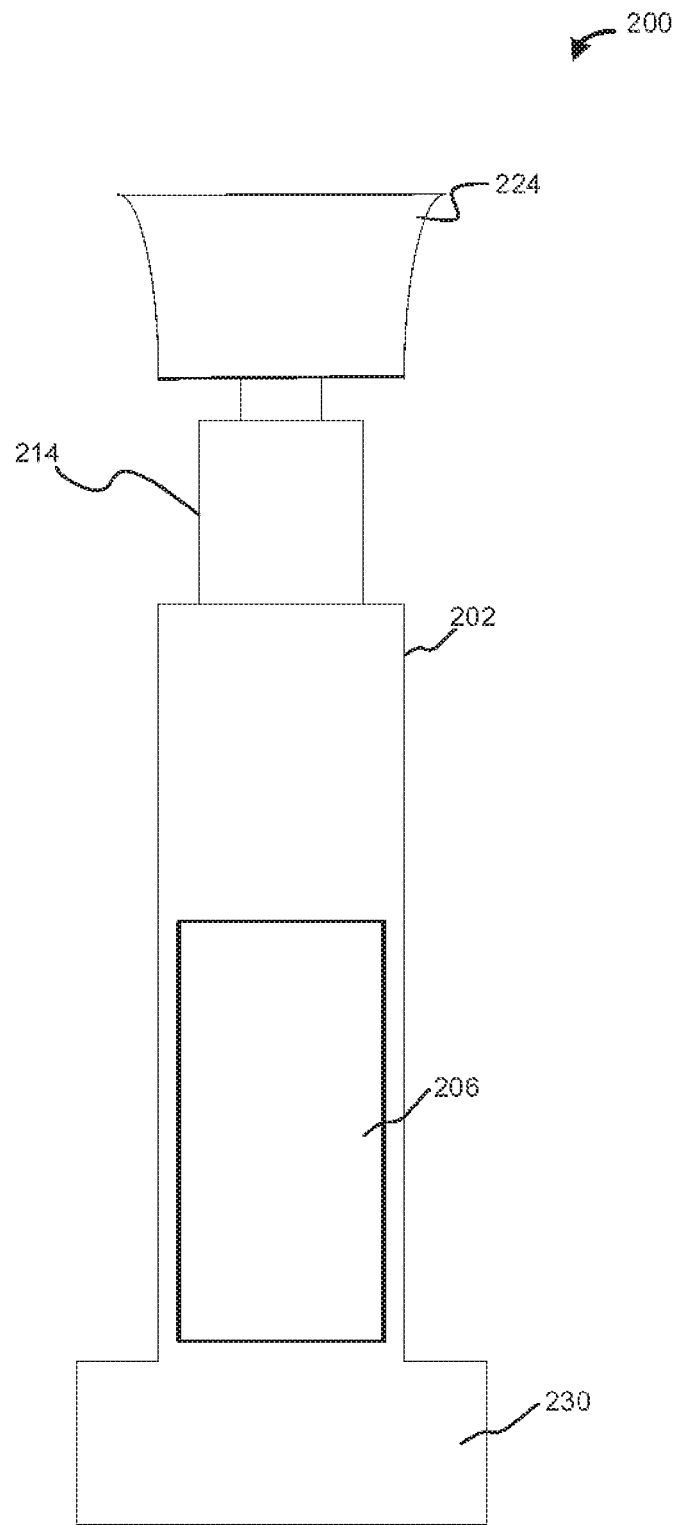
FIG. 3 shows a representative illustration of the vapor device configured for vaporizing water-based vaporizable liquid, as shown in FIG. 2.

FIG. 2 and FIG. 3 show an electronic vapor device 200 configured for vaporizing the disclosed vaporizable liquid as described herein. The electronic vapor device 200 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vapor device 200 can comprise any suitable housing 202 for enclosing and protecting the various components disclosed herein. The vapor device 200 can comprise a processor 204. The processor 204 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 204 can be printed or otherwise disposed on a circuit board. In some aspects, the circuit board and/or the processor can be formed using a polyimide such as Kapton, or other suitable temperature-resistant material. In other aspects, the processor 204 can comprise a standard eVapor device microprocessor. In still other embodiments, the processor 204 can comprise a hybrid microprocessor comprising elements of a Kapton-based printed microprocessor and a standard microprocessor. The processor 204 can be coupled (e.g., communicatively, operatively, etc. . . . ) to auxiliary devices or modules of the vapor device 200 using a bus or other coupling. The vapor device 200 can comprise a power supply 206. The power supply 206 can comprise one or more batteries and/or other power storage device (e.g., capacitor) and/or a port for connecting to an external power supply. For example, an external power supply can supply power to the vapor device 200 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like. In some aspects, power can be fed from the battery via an infrastructure comprising at least one of a conductive wire, other conductive material, a conductive metal, and other material, and wherein the infrastructure is configured to connect the battery to one or more powered elements of the vapor device 200.

The vapor device 200 can comprise a memory device 208 coupled to the processor 204. The memory device 208 can comprise a random access memory (RAM) configured for storing program instructions and data for execution or processing by the processor 204 during control of the vapor device 200. The memory device 208 can further comprise a long-term memory, for example, a non-volatile magnetic, optical, or electronic memory storage device, for storing program instructions and data when the vapor device 200 is powered off or in an inactive state. Either or both of the RAM or the long-term memory can comprise a non-transitory computer-readable medium storing program instructions that, when executed by the processor 204, cause the vapor device 200 to perform all or part of one or more methods and/or operations described herein. Program instructions can be written in any suitable high-level language, for example, C, C++, C# or Java™, and compiled to produce machine-language code for execution by the processor 204. The processor 204 can also be used to operate device system functions for one or more of usage meters, gauges, lights, sounds, skin effects, data readings, communications, ecommerce, medical care, and monitoring.

In some aspects, the connection between the power supply 206 and one or more of the powered elements (e.g., a dispersing element 212) can be facilitated using one or more conductive coils 210. The conductive coils 210 can provide an ultrasonic power input to the dispersing element 212. For example, the signal carried by the coil can have a frequency of approximately 107.8 kHz. In some aspects, the dispersing element 212 can comprise a piezoelectric dispersing element that can receive the ultrasonic signal transmitted from the power supply 206 through the coils 210, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid.

In an aspect, the vapor device 200 can comprise a dispersing element 212. In various aspects, the dispersing element 212 can comprise one or more of a piezoelectric dispersing element, a heated coil element, a standard eCigarette dispersion element, a modified vapor device heating element, and the like. The dispersing element 212 can be coupled to one or more containers 214 via a wick 216. Each of the one or more containers 214 can be configured to hold one or more vaporizable or non-vaporizable materials. The heating element 212 can receive the water-based liquid from the one or more containers 214 and disperse (e.g., atomize, form a mist or vapor) the water-based liquid until the water-based liquid achieves a vapor state.

The one or more containers 214 can be made of any suitable structural material, such as, an organic polymer, metal, ceramic, composite, or glass material. In some aspects, the one or more containers 214 can comprise one or more refillable containers, one or more disposable containers, and/or one or more replaceable containers. In various aspects, the one or more containers 214 can comprise internal structures 218 that provide antibacterial or antimicrobial protections. For example, the internal structures 218 can comprise at least one of silver strips and an ultraviolet (UV) light-emitting device. The one or more containers 214 can further comprise a mixing system 220 to enable even dispersal of components of the liquid within the container 214. In various embodiments, a pump 222 can facilitate transmission of the water-based liquid from the container 214 to the wick 216.

As described herein, the water-based liquid can comprise a liquid which, when vaporized produces a drastically reduced vapor cloud when compared to traditional eJuice or a liquid which, when vaporized, produces a substantially invisible vapor. In an aspect, the water-based liquid can be an eJuice having water as the primary compound therein. In some aspects, the water can be combined with one or more of a flavoring, nicotine, medication, wellness elements, aromatherapy elements (e.g., perfumes, flowers, spices, mint or aromas of a specific place and/or time, such as by way of example Fenway Park in Boston or Paris in the spring) and legal recreational elements in water soluble or controlled dispersal form. In some aspects, the water-based liquid can be substantially free of propylene glycol (PG) and/or vegetable glycerin (VG). The water can be distilled water, purified water, spring water, tap water, water subjected to reverse osmosis, heated water, water treated with vibrational frequencies including but not limited to sound, cooled water, or water treated with at least one other element.

A user can then draw on an outlet 224 to inhale the vapor. In some aspects, vapor exiting the dispersing element 212 toward the outlet 224 can flow through one or more grated exits 226 to facilitate dispersal of the vapor. In various aspects, the processor 204 can control vapor production and flow to the outlet 224. In some aspects the outlet 224 can comprise a mouthpiece. The mouthpiece can have a circumference greater than that of a traditional eVapor device mouthpiece. For example, the mouthpiece can have a circumference of approximately 0.75 inches. In some aspects, a seal 228 can be disposed between the dispersing element 212 and the outlet 224. The seal can be vapor-impermeable when the device is not in active use, and suction applied to the mouthpiece by the user can cause the seal to break temporarily, allowing flow of vapor through the outlet 224 for inhalation by the user.

In an aspect, the vapor device 200 can also comprise a transmitter 230 coupled to one or more of the processor 204, the dispersing element 212, and/or any other electronic component of the vapor device 200. Input can be received from a smart device 232 associated with the user In some aspects, the transmitter 230 can comprise an interface port such as a wired interface, for example a serial port, a Universal Serial Bus (USB) port, an Ethernet port, or other suitable wired connection. In some aspects, the transmitter 230 can comprise a wireless interface, for example a transceiver using any suitable wireless protocol, for example WiFi (IEEE 802.11), Bluetooth®, infrared, or other wireless standard. For example, transmitter 230 can communicate with a smartphone via Bluetooth® such that the inputs and outputs of the smartphone can be used by the user to interface with the vapor device 200.

Input from the transmitter 230 can be used by the processor 204 to cause the dispersing element 212 to vaporize the water-based vaporizable liquid. For example, a user can depress a button, causing the dispersing element 212 to start vaporizing the water-based vaporizable liquid. In some aspects, the transmitter 230 can be used to receive user information (e.g., from the user smart device 232). The user information can be verified by the processor 204. The vapor device 200 and/or the smart device 232 can comprise software for verifying the user data.

In an aspect, illustrated in FIG. 4, provided is method 400 comprising receiving disclosed vaporizable liquid at a dispersing element at 402. In some aspects the water-based vaporizable liquid can comprise a liquid which, when vaporized produces a drastically reduced vapor cloud when compared to traditional eJuice or a liquid which, when vaporized, produces a substantially invisible vapor. In an aspect, the water-based vaporizable liquid can be an eJuice having water as the primary compound therein. In some aspects, the water can be combined with one or more of a flavoring, nicotine, medication, wellness elements, aromatherapy elements (e.g., perfumes, flowers, spices, mint or aromas of a specific place and/or time, such as by way of example Fenway Park in Boston or Paris in the spring) and legal recreational elements in water soluble or controlled dispersal form to form the water-based vaporizable liquid. In some aspects, the water-based vaporizable liquid can be substantially free of propylene glycol (PG) and/or vegetable glycerin (VG). The water can be distilled water, purified water, spring water, tap water, water subjected to reverse osmosis, heated water, water treated with vibrational frequencies including but not limited to sound, cooled water, or water treated with at least one other element. In some aspects, the water-based vaporizable liquid is received from a container, such as a refillable, replaceable, and/or disposable container.

In some aspects, the dispersing element (e.g., the vaporizer 108) can comprise, for example, a piezoelectric dispersing element. The piezoelectric dispersing element can comprise a thin metal disc which disperses (e.g., atomizes, vaporizes) the fluid fed into the dispersing element. In other aspects, the dispersing element can comprise a heated coil element, a standard eCigarette dispersing element, a modified vapor device heating element or the like. The water-based vaporizable liquid can be received at the dispersing element via, for example, a wick or other soaked piece of organic material, or other disbursement mechanism such as a perforated nozzle.

The water-based vaporizable liquid can be vaporized (e.g., dispersed, atomized) at 404, resulting in a vapor. For example, the water-based vaporizable liquid can be dispersed by the dispersing element. The vapor can then be expelled through an exhaust port at 406 for inhalation by a user. In some aspects, the exhaust port can comprise one or more of a plurality of grated exits configured to facilitate the dispersal of vapor, a single opening, and a pump and perforated nozzle system configured to project vapor.

In some aspects, the method 400 can further comprise verifying user information prior to dispersing the water-based vaporizable liquid. For example, a transmission comprising user information can be received and compared to verification information. The user information can comprise, for example, user identification information, age information, and the like. The verification information can comprise, for example, information identifying a user that purchased a device and an age of that user. In other aspects, the verification information can further comprise an age required for consumption of nicotine-based eJuice.

In view of the exemplary systems and methods described supra, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

Various aspects presented in terms of systems can comprise a number of components, modules, and the like. It is to be understood and appreciated that the various systems may include additional components, modules, etc. and/or may not include all of the components, modules, etc. discussed in connection with the figures. A combination of these approaches can also be used.

In addition, the various illustrative logical blocks, modules, and circuits described in connection with certain aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC or may reside as discrete components in another device.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Those skilled in the art will recognize many modifications may be made to this configuration without departing from the scope of the disclosed aspects.

F. Kits

In one aspect, disclosed are kits comprising a vaporizable liquid composition comprising: (a) at least one solvent comprising water, a water-based solution, an alcohol, or a combination thereof; and (b) at least one agent selected from a pharmaceutical composition, a nutraceutical composition, and a plant extract, wherein the vaporizable liquid composition is substantially free of propylene glycol (PG) and vegetable glycerin (VG), and one or more of: (c) an electronic vapor device; and (d) at least one additive selected from a flavorant, a wellness element, a recreational element, a medicinal element, an emulsifier, a surfactant, and a stabilizer.

In a further aspect, the solvent and the at least one agent are co-formulated. In a further aspect, the solvent and the at least one agent are co-packaged.

In a further aspect, the solvent and the at least one additive are co-formulated. In a further aspect, the solvent and the at least one additive are co-packaged.

In a further aspect, the at least one agent and the at least one additive are co-formulated. In a further aspect, the at least one agent and the at least one additive are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

The previous description of the disclosed aspects is provided to enable any person skilled in the art to make or use the present disclosure. Various modifications to these aspects will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow;

plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A personal vaporizer comprising:
    a device processor operable for controlling the personal vaporizer, wherein the device processor is operable to generate an activation command to initiate a vaporization process;
    a container configured to store a water-based vaporizable liquid composition, wherein the water-based vaporizable liquid composition comprises at least one monitored compound;
    a dispersing component operatively coupled to the device processor and controlled in part by the device processor, wherein the dispersing component is in fluid communication with the container for receiving at least a portion of the selected amount of the water-based vaporizable liquid composition from the container, wherein the dispersing component is operable to vaporize at least a portion of the water-based vaporizable liquid composition received therein;
    a vapor outlet coupled to the dispersing component and configured to receive a vapor generated by the dispersing component, the vapor outlet operable to expel the generated vapor from the dispersing component;
    an input/output device operatively coupled to the device processor; wherein the input/output device is configured to receive a plurality of data for transmission to the device processor, wherein the input/output device is configured to transmit a plurality of data generated by the device processor; and
    a power source operatively coupled to the dispersing component, wherein the power source is operable to generate a supply of power for operation of the dispersing component;
    wherein the device processor is further operable to,
        receive a plurality of user data associated with a user of the personal vaporizer, wherein the plurality of user data includes at least one of user identification data, user age data, and combinations thereof;
        generate, based on at least a portion of the plurality of the user data, at least one device activation control signal; and
        transmit the at least one device activation control signal to the dispersing component to initiate the vaporization process in accordance with the at least one device activation control signal.

2. The personal vaporizer of claim 1, wherein the dispersing component comprises an ultrasonic vibration element operable to produce ultrasonic vibrations to vaporize at least a portion of the water-based vaporizable liquid composition received therein.

3. The personal vaporizer of claim 2, wherein the device processor is further operable to:
    receive user verification data, wherein the user verification data includes at least one of device purchaser identification data, usage age data, and combinations thereof; and
    compare the received user data to the user verification data to determine whether the user data matches the user verification data.

4. The personal vaporizer of claim 3, wherein the device processor is further operable to:
    generate, based on a determination that the user data matches the user verification data, at least one device activation control signal to initiate the vaporization process; and
    generate, based on a determination that the user data does not match the user verification data, at least one device activation control signal to restrict initiation of the vaporization process.

5. The personal vaporizer of claim 3, wherein the usage age data comprises data associated with a minimum age for use of the personal vaporizer.

6. The personal vaporizer of claim 5, wherein the minimum age for use of the personal vaporizer is based on the at least one monitored compound contained in the water-based vaporizable liquid composition stored in the container.

7. The personal vaporizer of claim 1, wherein the at least one monitored compound is a cannabinoid compound.

8. The personal vaporizer of claim 1, wherein the cannabinoid compound is selected from the group consisting of cannabidiol (CBD), tetrahydrocannabinol (THC), cannabinol (CBN), and combinations thereof.

9. The personal vaporizer of claim 1, wherein the input/output device comprises a user interface, wherein the device processor is operable to receive at least a portion of the plurality of user data from an associated user via the user interface.

10. The personal vaporizer of claim 1, wherein the input/output device is configured to receive at least a portion of the plurality of user data from a remote device.

11. A method for activating a personal vaporizer to initiate a vaporization process, the personal vaporizer comprising,
    (a) a device processor operable for controlling the personal vaporizer;
    (b) at least one container configured to store a water-based vaporizable liquid composition, wherein the water-based vaporizable liquid composition comprises at least one monitored compound;
    (c) a dispersing component comprising dispersing element operable to vaporize at least a portion of the water-based vaporizable liquid composition received therein;
    d) a vapor outlet operable to expel the generated vapor from the dispersing component;
    (e) an input/output device configured to receive a plurality of data for transmission to the device processor and to transmit a plurality of data generated by the device processor; and
    (f) a power source operable to generate a variable strength electrical current for operation of the dispersing component, the method comprising:
    receiving, at the device processor, a plurality of user data associated with a user of the personal vaporizer, wherein the plurality of user data includes at least one of user identification data, user age data, and combinations thereof;
    generating, by the device processor, based on at least a portion of the plurality of the user, at least one device activation control signal;
    transmitting the at least one device activation control signal to the ultrasonic vaporizing component to initiate the vaporization process in accordance with the at least one device activation control signal; and initiating, by the ultrasonic vaporizing component, a vaporization process to vaporizer at least a portion of the water-based vaporizable liquid composition.

12. The method of claim 11, further comprising:
receiving, at the device processor, user verification data, wherein the user verification data includes at least one of device purchaser identification data, usage age data, and combinations thereof; and
comparing, by the device processor, the received user data to the user verification data to determine whether the user data matches the user verification data.

13. The method of claim 12, further comprising generating, by the device processor, based on a determination that the user data matches the user verification data, at least one device activation control signal to initiate the vaporization process.

14. The method of claim 12, further comprising generating, by the device processor, based on a determination that the user data does not match the user verification data, at least one device activation control signal to restrict initiation of the vaporization process.

15. The method of claim 12, wherein the usage age data comprises data associated with a minimum age for use of the personal vaporizer.

16. The method of claim 15, wherein the minimum age for use of the personal vaporizer is based on the at least one monitored compound contained in the water-based vaporizable liquid composition stored in the least one container.

17. The method of claim 11, wherein the at least one monitored compound is a cannabinoid compound.

18. The method of claim 11, wherein the cannabinoid compound is selected from the group consisting of cannabidiol (CBD), tetrahydrocannabinol (THC), cannabinol (CBN), and combinations thereof.

19. The method of claim 11, further comprising receiving at least a portion of the plurality of user data from an associated user via the input/output device.

20. The method of claim 11, further comprising receiving at least a portion of the plurality of user data from a remote device via the input/output device.

* * * * *